United States Patent [19]

Lutz et al.

[11] Patent Number: 5,246,915

[45] Date of Patent: Sep. 21, 1993

[54] METHOD FOR CONTROLLING WEEDS

[75] Inventors: William R. Lutz, Riehen, Switzerland; Guy R. E. Van Lommen, Berlaar; Jozef F. E. Van Gestel, Vosselaar, both of Belgium

[73] Assignee: Janssen Pharmaceutica N.V., Beerse, Belgium

[21] Appl. No.: 842,301

[22] Filed: Feb. 26, 1992

Related U.S. Application Data

[63] Continuation of Ser. No. 330,962, Mar. 29, 1989, Pat. No. 4,996,184, which is a continuation of Ser. No. 137,385, Dec. 23, 1987, abandoned, which is a continuation-in-part of Ser. No. 944,282, Dec. 19, 1986, abandoned, which is a continuation-in-part of Ser. No. 876,532, Jun. 20, 1986, abandoned.

[51] Int. Cl.$^5$ .................... A01N 43/48; C07D 233/66
[52] U.S. Cl. ................ 504/279; 548/334.5; 548/322.5; 548/311.4
[58] Field of Search .............. 548/343; 504/279

[56] References Cited

U.S. PATENT DOCUMENTS 3,485,917 12/1969 Godefroi et al. .................. 424/273
3,873,297  3/1975 Kupelian ............................. 71/78
4,182,624  1/1980 Soder et al. ......................... 71/92

*Primary Examiner*—Johann Richter
*Attorney, Agent, or Firm*—Charles J. Metz

[57] ABSTRACT

A method for controlling weeds preferably in the crops of useful plants by using a 5-imidazolecarboxylic acid derivative; herbicidal compositions containing the same; novel 5-imidazolecarboxylic acid derivatives.

13 Claims, No Drawings

METHOD FOR CONTROLLING WEEDS

This is a continuation of copending application Ser. No. 330,962, filed Mar. 29, 1989 now U.S. Pat. No. 4,996,184 which was a continuation of application Ser. No. 137,385, filed Dec. 23, 1987, (now abandoned), which was a continuation-in-part of application Ser. No. 944,282, filed Dec. 19, 1986, (now abandoned) which in turn was a continuation-in-part of application Ser. No. 876,532, filed Jun. 20, 1986 (now abandoned).

BACKGROUND OF THE INVENTION

Some of the active ingredients for use in the method for controlling weeds according to the present invention, methods of preparing same and their pharmaceutical use as antifungal agents are known from U.S. Pat. No. 3,485,917. Further, some of these compounds were described as active agents in a method for inhibiting bud growth in U.S. Pat. No. 3,873,297. The majority of compounds of formula (I) are novel and have especially been developed to be used in the method of this invention.

SUMMARY OF THE INVENTION

The present invention relates to a novel method for controlling weeds, preferably selectively in crops of useful plants. Further, the invention also relates to novel compounds used in said new method; to processes for preparing these compounds and to compositions containing them as active ingredients.

DETAILED DESCRIPTION OF THE INVENTION

According to the method of the present invention weeds can be controlled by applying thereto or to the locus thereof of a herbicidally effective amount of a 5-imidazolecarboxylic acid derivative of formula

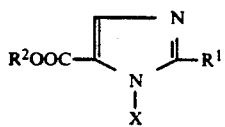

(I)

or a stereochemically isomeric form thereof, or of a salt thereof, wherein $R^1$ is hydrogen or mercapto, $R^2$ is hydrogen, $C_1$–$C_7$ alkyl, $C_3$–$C_7$ alkenyl, $C_3$–$C_7$ alkynyl, $C_1$–$C_7$alkoxy-$C_1$–$C_7$alkyl, aryl-$C_1$–$C_5$alkyl or $C_3$–$C_7$cycloalkyl and X is 1-indanyl, 1-tetrahydronaphthalenyl, 5-benzocycloheptanyl, 4-tetrahydrobenzothienyl, 4-tetrahydrobenzofuryl, 5-tetrahydroquinolyl, 5-tetrahydroisoquinolyl, 8-tetrahydroquinolyl, 8-tetrahydroisoquinolyl, 9,10-dihydro-9-anthracenyl, 9H-fluoren-9-yl, 5-dibenzo[a,d]cycloheptenyl, 5-dibenzo[a,d]cycloheptanyl or 1-dihydronaphthalenyl each unsubstituted or substituted with one to six substituents selected from the group consisting of $C_1$–$C_5$alkyl, mono-and di(aryl) $C_1$–$C_5$alkyl, $C_1$–$C_5$alkoxy, halo, $C_3$–$C_7$alkenyl, amino, nitro, $C_1$–$C_6$alkylcarbonylamino, trifluoromethyl and difluoromethoxy, wherein two geminal substituents together with the carbon atom to which they are attached may form a $C_3$–$C_7$cycloalkyl group; wherein aryl is phenyl optionally substituted with one to three substituents each independently selected from the group consisting of $C_1$–$C_5$alkyl, $C_1$–$C_5$alkyloxy and halo.

Suprisingly, the compounds of formula (I) exhibit strong herbicidal properties, and are therefore useful to control weeds. This property gains importance by the fact that some crops of useful plants are not damaged, or are only slightly harmed when treated with compounds of formula (I) at high dosages. Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment.

The active ingredients of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.02 kg and 1.0 kg a.i. per hectare.

As used in the foregoing definitions $C_1$–$C_5$alkyl denotes straight or branch chained saturated hydrocarbon radicals having from 1 to 5 carbon atoms, e.g. methyl, ethyl, propyl, isopropyl, the four butyl isomers, the pentyl isomers; $C_1$–$C_7$alkyl includes $C_1$–$C_5$alkyl radicals and the higher homologs thereof having 6 or 7 carbon atoms; halo is fluoro, chloro, bromo or iodo, with fluoro and chloro being preferred;

$C_3$–$C_7$alkenyl straight and branched chained hydrocarbon radicals containing one double bond and having from 3 to 7 carbon atoms such as, for example, allyl, 3-butenyl, 2-butenyl, 2-pentenyl, 3-pentenyl, methallyl, or 3-methyl-2-butenyl, with allyl and methallyl being preferred;

$C_3$–$C_7$alkynyl defines straight and branch chained hydrocarbon radicals containing one triple bond and having from 3 to 7 carbon atoms such as, for example, propargyl, 2-butynyl, 3-butynyl, 2-pentynyl, 3-pentynyl or 4-pentynyl, with propargyl being preferred;

$C_3$–$C_7$cycloalkyl is generic to cyclopropyl, cyclobutyl, cyclopentyl, cyclohexyl and cycloheptyl, with cyclopentyl and cyclohexyl being preferred.

As typical examples of the aryl defined hereinabove, there may be mentioned phenyl, 4-chlorophenyl, 4-fluorophenyl, 2,4-dichlorophenyl, 4-methoxyphenyl, 4-methylphenyl, 3-chlorophenyl, 3,4-dimethoxyphenyl, 2,5-dichlorophenyl, 2,4-dimethoxyphenyl.

As examples of aryl-$C_1$–$C_5$-alkyl or diaryl-$C_1$–$C_5$alkyl groups there may be mentioned benzyl, phenylethyl, 4-chlorobenzyl, 4-chlorophenylethyl, benzhydryl, 4-methoxybenzyl, 3-methoxybenzyl, or 4,4'-dichlorobenzhydryl, benzyl and benzhydryl being preferred. $C_1$–$C_5$alkoxy denotes, for example, methoxy, ethoxy, n-propyloxy, isopropyloxy, the four butyloxy isomers or the pentyloxy isomers; $C_1$–$C_7$alkoxy $C_1$–$C_7$alkyl denotes for example methoxymethyl, methoxyethyl, methoxypropyl, ethoxymethyl, ethoxyethyl, ethoxypropyl, propoxymethyl, propoxyethyl, propoxypropyl, isopropoxymethyl isopropoxyethyl, isopropoxypropyl, 2-methoxypropyl, 2-ethoxypropyl, 2-methoxybutyl, 3-methoxybutyl, 2-ethoxybutyl, or 3-ethoxybutyl.

It is evident that the substituents on the radical X may be attached to different carbon atoms, or two of them may also take geminal positions.

Depending on the nature of the moiety X and/or the group $R^2$ the compounds of formula (I) may contain asymmetrical carbon atoms. Unless otherwise mentioned or indicated, the chemical designation of compounds denotes the mixtures of all stereochemically isometric forms. These mixtures contain all diastereomers and enantiomers of the basic molecular structure.

The absolute configuration of each chiral center may be indicated by the stereochemical descriptors R and S, this R and S notation corresponding to the rules described in Pure Appl. Chem. 1976, 45, 11-30. The relative configuration of the asymmetric centers in the compounds of formula (I) is denoted by cis and trans and where appropriate by the terms α and β, these stereochemical descriptors being used according to the rules described in Chemical Abstracts 1977 Index Guide, Appendix IV, §203.

In some compounds the stereochemical configuration is not experimentally determined. In those cases it is conventionally agreed to designate the stereochemically isomeric form which is first isolated as "A" and the second as "B", without further reference to the actual stereochemical configuration.

In some compounds of formula (I) the rotation around the carbon-nitrogen bond linking the X moiety and the imidazole nucleus, may be highly hindered. Consequently, such compounds may occur as atropisomers, said atropisomers being comprised within the scope of the present invention. The atropisomer which is first isolated is defined as atropisomer A and the second as atropisomer B, without further reference to the actual conformation.

Pure isomeric forms of these compounds can be separated from the mixtures by conventional separation methods. Preferably, if a specific stereochemical form is desired, said compound will be synthesized by stereoselective methods of preparation. These methods will advantageously employ optically active starting materials.

The invention also comprises the use of the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples for salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are toluenesulfonic acid, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorous containing acids are the various phosphonous acids, phosphonic acids and phosphonic acids.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and teritary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2,2,2]octane being most preferred. Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

A preferred subgroup of active ingredients used in the method of this invention are those compounds of formula (I), wherein $R^2$ is hydrogen, $C_1$-$C_7$alkyl, $C_3$-$C_7$alkenyl, $C_3$-$C_7$alkynyl or $C_3$-$C_7$cycloalkyl, and X is 1-indanyl, 1-tetrahydronaphthalenyl or 5-benzocycloheptanyl, each unsubstituted or substituted with one to six substituents independently selecetd from $C_1$-$C_5$alkyl, $C_1$-$C_5$alkoxy, halo, trifluoromethyl or difluoromethoxy.

Within this preferred group, those compounds are particularly preferred, wherein X is a radical of formula:

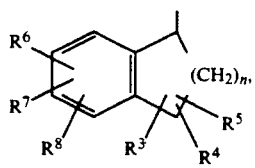

(a)

wherein
$R^3$, $R^4$ and $R^5$ are each independently hydrogen or $C_1$-$C_5$alkyl, $R^6$, $R^7$ and $R^8$ are each independently hydrogen or $C_1$-$C_5$alkyl, $C_1$-$C_5$alkoxy, halo, $CF_3$ or $OCHF_2$, and
n is 1 or 2 or 3.

Within this group of particularly preferred compounds special preference is put to compounds wherein either
a) n is two or
b) n is one or
c) $R^3$, $R^4$ and $R^5$ are each independently hydrogen or methyl or
d) $R^6$, $R^7$ and $R^8$ are each independently hydrogen, methyl, methoxy, fluoro, chloro or bromo or
e) $R^2$ is $C_1$-$C_4$alkyl.

From subgroup e) those compounds are preferred wherein $R^2$ is methyl.

A more particularly preferred subgroup comprises those compounds wherein n is two, $R^3$, $R^4$ and $R^5$ are each independently hydrogen or methyl, $R^6$, $R^7$ and $R^8$ are each independently hydrogen, methyl, methoxy, fluoro, chloro or bromo, and $R^2$ is $C_1$-$C_4$alkyl. Among this group again those compounds are preferred, wherein $R^2$ is methyl.

The same preference is given to compounds wherein n is one, $R^3$, $R^4$ and $R^5$ are each independently hydrogen or methyl, $R^6$, $R^7$ an $R^8$ are each independently hydrogen, methyl, methoxy, fluoro, chloro or bromo, and $R^2$ is $C_1$-$C_4$alkyl.

The most preferred compounds which can be used in the method according to this invention are selected among 1-(1,2,3,4-tetrahydronaphthalen-1-yl)-5-imidazolecarboxylic acid methyl ester, 1-(2-methyl-1,2,3,4-tetrahydronaphthalen-1-yl)-5-imidazolecarboxylic acid methyl ester, 1-(2,2-dimethyl-1,2,3,4-tetrahydronaphthalen-1-yl)-5-imidazolecarboxylic acid methyl ester, 1-(5,7-dimethyl-1,2,3,4-tetrahydronaphthalen-1-yl)-5-imidazolecarboxylic acid methyl ester, 1-(2,2-dimethylindan-1-yl)-2-mercapto-5-imidazolecarboxylic acid methyl ester, 1-(1R-2,2-dimethylindan-1-yl)-5-imidazolecarboxylic acid methyl ester, 1-(2,2-dimethylindan-1-yl)-5-imidazolecarboxylic acid methyl ester;

1-(fluoren-9-yl)-5-imidazolecarboxylic acid methyl ester, the salts and possible stereoisomeric forms of thereof.

As mentioned above most of the active ingredients of formula (I) are novel compounds and have especially been developed to be used as active substances in the novel method for controlling weeds according to the present invention. These compounds therefore constitute a further aspect of the invention. The said novel compounds can be represented by the formula

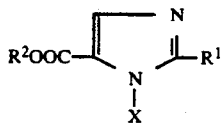

(I')

wherein, $R^1$, $R^2$ and X have the previously defined meaning, provided that X is other than unsubstituted 1-indanyl, or unsubstituted 1-tetrahydronaphthalenyl.

Preferred novel compounds are those wherein X is a radical of formula (a) as defined hereinabove, wherein n is one, $R^3$, $R^4$ and $R^5$ are each independently hydrogen or methyl, $R^6$, $R^7$ and $R^8$ are each independently hydrogen, methyl, methoxy, fluoro, chloro or bromo, and $R^2$ is $C_1$–$C_4$alkyl.

The most preferred novel compounds are:

1-(2-methyl-1,2,3,4-tetrahydronaphthalen-1-yl)-5-imidazolecarboxylic acid methyl ester.

1-(2,2-dimethyl-1,2,3,4-tetrahydronaphthalen-1-yl)-5-imidazolecarboxylic acid methyl ester, 1-(5,7-dimethyl-1,2,3,4-tetrahydronaphthalen-1-yl)-5-imidazolecarboxylic acid methyl ester, (2,2-dimethylindan-1-yl)-2-mercapto-5-imidazolecarboxylic acid methyl ester, 1-(1R-2,2-dimethylindan-1-yl)-5-imidazolecarboxylic acid methyl ester, 1-(2,2-dimethylindan-1-yl)-5-imidazolecarboxylic acid methyl ester, 1-(fluoren-9-yl)-5-imidazolecarboxylic acid methyl ester, the salts and stereoisomeric forms thereof.

The preparation of the compounds of formula (I), both the novel ones and the known ones, is generally carried out by the following methods.

The compounds of formula (I) can be obtained by condensing a compound of formula

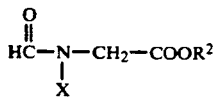

(II)

wherein $R^2$ and X are as defined hereinabove, with a $C_1$–$C_4$alkyl ester of formic acid in the presence of suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

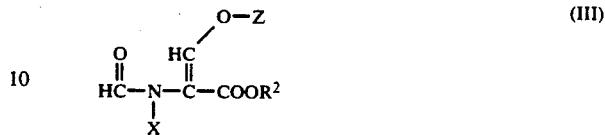

(III)

wherein $R^2$ and X are as defined hereinabove and Z is an alkali metal atom.

a) with an alkali metal isothiocyanate in the presence of an acid, thus obtaining a 2-mercaptoimidazole of formula

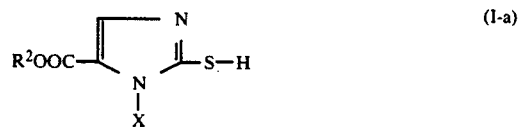

(I-a)

wherein $R^2$ and X are as defined hereinabove, which optionally is converted into a compound of the formula

(I-b)

by reacting the starting compound with nitric acid optionally in the presence of an alkali metal nitrite, e.g. sodium nitrite; or with Raney-nickel in the presence of a lower aliphatic alcohol, preferably ethanol, at a temperature between 40° C. and 80° C.; or also by treating the starting compounds with an aqueous hydrogen peroxide solution preferably in the presence of a carboxylic acid, e.g. acetic acid; or b) with a carboxylic acid amide of 1 to 3 carbon atoms, preferably formamide, in the presence of an acid at a temperature between 50° C. and 250° C., preferably between 120° C. and 170° C.; or c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example 1,1'-oxybisethane, tetrahydrofuran of 1,4-dioxane; or other aprotic organic solvents. For the cyclization-reaction of the imidazole ring structure, strong mineral acids such as hydrohalic acids, e.g. hydrochloric acid, are most conveniently employed. In the ring-forming variant c) also other acids, e.g. acetic acid, can be used.

In this reaction an excess of acid of 5 to 50, preferably of 15 to 40 times the required molar amount is most preferably used. The excess of ammonium salt in this process is 2 to 50, preferably 10 to 30 times the required molar amount.

The compounds of formula (I-b) can also be prepared by the deamination reaction of a 4-amino-1H-imidazole derivative of formula (IV), wherein $R^2$ and X are as defined under formula (I). Said deamination reaction involves a diazotation and reductive dediazotation step which may be conducted sequentially, i.e. with isolation of the intermediate diazonium salt (IV-a) or in a one-pot fashion wherein said diazonium salt is reduced in situ.

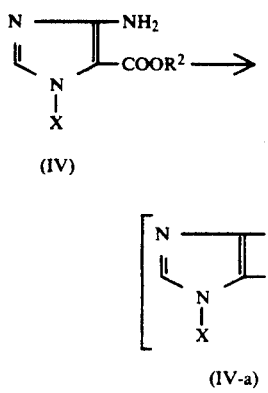

Treatment of the 4-amino-1H-imidazole derivative of formula (IV) in aqueous medium with an alkali metal nitrite, e.g. sodium or potassium nitrite, in the presence of an acid such as hydrochloric acid, sulfuric acid or nitric acid, or with nitronium tetrafluoroborate ($NO^+BF_4^-$) yields the diazonium salt (IV-a). In the latter, $R^2$ and X are as defined under formula (I) and $A^-$ represents an anion corresponding to the conjugated base of the acid employed in the diazotation reaction or the tetrafluoroborate anion. The intermediate diazonium salts (IV-a) are reduced to the compounds of formula (I-b) by treatment with an appropriate reductant such as hypophosphoric acid at an elevated temperature, preferably at the boiling temperature of the reaction mixture.

Alternatively, treatment of the 4-amino-1H-imidazole derivatives of formula (IV) with a $C_{1-5}$alkyl nitrite such as, 1,1-dimethylethyl nitrite of 3-methylbutyl nitrite in a suitable aprotic solvent such as tetrahydrofuran, 1,4-dioxane, trichloromethane or N,N-dimethylformamide yields a compound of formula (I-b) directly. The latter deamination reaction may conveniently be conducted at an elevated temperature, generally at the boiling point of the reaction mixture.

The compounds of formula (I) can also be converted into each other following art-known functional group transformation reactions. The substituent $R^2$ on the carboxylic acid group may be transformed to other substituents encompassed by the definition of $R^2$ by suitable reactions known in the art for the modification of carboxylic acid functions, e.g. by hydrolysis and esterification and/or transesterification.

If the synthesis of sterochemically pure isomers is intended, stereoselective reaction steps and conditions are recommended. On the other hand conventional methods of separation can be used for obtaining pure isomers from a mixture of stereochemical isomers.

Some of the starting materials for the preparation of the compounds of formula (I) are known, while others are new and can be obtained by known synthesis procedures.

For example, the compounds of formula (II) can be obtained by N-formylating a glycine ester of formula $$X-NH-CH_2-COOR^2 \qquad (V)$$

wherein $R^2$ and X are as defined hereinabove, with formic acid in the presence of acetic anhydride. In turn, the compounds of formula (V) can be prepared by N-alkylation an amine of formula $$X-NH_2 \qquad (VI)$$

wherein X is as defined under formula (I), with an α-haloacetic acid ester, e.g. α-bromaacetic ester, of formula $$Br-CH_2-COOR^2 \qquad (VII)$$

wherein $R^2$ is as defined under formula (I). The reaction of (VI) with (VII) is conveniently conducted in a reaction-inert solvent, e.g. tetrahydrofuran, 1,1'-oxybisethane, N,N-dimethylformamide or dichloromethane, in the presence of a base such as an alkali metal carbonate, e.g. sodium carbonate.

The 4-amino-1H-imidazole derivatives of formula (IV) can be obtained by cyclizing an intermediate of formula $$NC-N=CH-N-CH_2-COOR^2 \qquad (VIII)$$
$$\phantom{NC-N=CH-N-}|$$
$$\phantom{NC-N=CH-N-}X$$

wherein X and $R^2$ are as defined hereinabove under catalysis of a base at elevated temperature in a suitable solvent, e.g. an alcohol. A preferred mode of carrying out said cyclization may comprise the reaction of the starting compound (VIII) in an alcohol, preferably that alcohol of which the ester group $COOR^2$ is derived, in the presence of a catalytic amount of alkoxide obtained by dissolving an alkali metal in said alcohol, at the boiling point of the reaction mixture. Or, alternatively, by reacting (VIII) with an alkali metal alkoxide wherein the alkoxide preferably is $OR^2$ in a polar solvent such as N,N-dimethylformamide or dimethyl sulfoxide. Generally, the reaction temperatures are in the range of +60° C. to +140° C.

The intermediates of formula (VIII) in turn can be prepared by alkylating an amidine of formula $$NC-N=CH-NH-X \qquad (IX)$$

wherein X is as defined under formula (I) with an α-haloacetic acid ester of formula (VII), in the presence of an appropriate base, such as, for example an alkali metal hydroxide, an alkali or earth alkaline metal carbonate or hydrogen carbonate, an earth alkaline oxide, an alkali metal alkoxide or a trialkylamine, e.g. sodium hydroxide, potassium hydroxide, sodium carbonate, potassium hydrogen carbonate, magnesium oxide, calcium oxide, sodium methoxide, sodium ethoxide, potassium ethoxide, potassium isopropoxide, pyridine, N,N-diethylethanamine and the like. In some instances, the addition of a crown-ether may be recommendable. The reaction may conveniently be conducted at temperatures between +10° C. and the boiling point of the reaction mixture, either without a solvent or in a solvent such as N,N-dimethylformamide, N,N-dimethylacetamide or dimethyl sulfoxide.

The compounds of formula (IX) can be prepared by reacting an amine of formula (VI) with a $C_{1-5}$alkyl-N-cyanomethanimidate of formula

$$C_{1-5}alkyl-O-CH=N-CN \quad (X)$$

in an appropriate reaction-inert solvent such as trichloromethane, tetrahydrofuran, 1,4-dioxane, acetonitrile, N,N-dimethylformamide or N,N-dimethylacetamide. The said reaction can conveniently be carried out at temperatures between room temperature and the boiling point of the reaction mixture, in particular between +20° C. and +80° C. Removal of the $C_{1-5}$alkanol which is liberated during the course of the reaction and of the solvent by destillation under reduced pressure yields the N-cyanoamidine of formula (IX) which in general need not be purified before further convertion.

The 4-amino-1H-imidazole derivatives of formula (IV) can alternatively be obtained from the amines of formula (VI), by a combined N-alkylating and cylclization reaction in a one-pot procedure. The latter procedure is conducted in the same solvents and bases as mentioned hereinabove for the two step synthesis.

The amines of formula (VI) can be obtained by the reduction of an oxime of formula $$X^1=N-OH \quad (XI),$$

wherein $X^1$ is a geminal bivalent radical obtained by abstracting a further hydrogen atom from the carbon atom which links the X-radical with the 1H-imidazole-5-carboxylic acid group. Said reduction is conveniently conducted with hydrogen in the presence of a noble metal catalyst or with a metallic hydride reagent, e.g. lithium tetrahydroaluminate or diborane in a suitable reaction-inert solvent such as an ether, e.g. tetrahydrofuran, 1,4-dioxane and the like. The oxime of formula (XI) may also be reduced electrochemically.

Said oxime (XI) in turn, can be prepared from the corresponding ketone of formula $$X^1=O \quad (XII)$$

wherein $X^1$ is as defined hereinabove, by reacting said ketone of formula (XII) with hydroxylamine.

The amines of formula (VI) can also be prepared by the reductive amination of a ketone of formula (XII) with formamide in the presence of formic acid and subsequent removal of the N-formyl group by treatment with a hydrohalic acid, e.g. hydrochloric acid.

The intermediates of formula (V) can also be obtained by the reductive N-alkylation reaction of a ketone of formula (XII) with an glycine ester derivative (XIII), wherein $X^1$ and $R^2$ are as defined hereinabove.

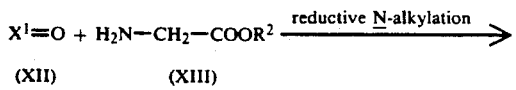
$$X^1=O + H_2N-CH_2-COOR^2 \xrightarrow{\text{reductive N-alkylation}}$$
$$(XII) \quad (XIII)$$

-continued
$$X-NH-CH_2-COOR^2$$
$$(V)$$

Said reductive N-alkylation reaction may conveniently be carried out by hydrogenating a stirred and, if desired, heated mixture of the reactants in a suitable reaction-inert organic solvent according to art-known catalytic hydrogenating procedures. Suitable solvents are, for example, alkanols, e.g. methanol, ethanol; ethers, such as tetrahydrofuran. The term "art-known catalytic hydrogenating procedures" means that the reaction is carried out under hydrogen atmosphere and in the presence of a catalyst such as, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g. thiopene.

Alternatively, said reductive N-alkylation reactions may be conducted by treating a stirred and, if desired, heated mixture of the reactants with sodium cyanoborohydride, sodium borohydride, formic acid or a salt thereof, e.g. ammonium formiate.

Typical preparation methods of the ketones of formula (XII) are described in e.g. J. Am. Chem. Soc. 1952, 74, 1259; J. Am. Chem. Soc. 1971, 93, 2432; J. Org. Chem. 1968, 33, 1480 and J. Org. Chem. 1968, 33, 1489.

The compounds of formula (I) are stable compounds and no precautionary measures are required for handling them.

When used at the indicated rates of application, the compounds of formula (I) have good selective herbicidal properties which make them most suitable for use in crops of useful plants, preferably in maize and in rice. In some cases damage is also caused to weeds which up to now have only been controlled up to now with total herbicides.

At higher rates of application, all tested plants are so severely damaged in their development that they die.

The invention also relates to herbicidal compositions which contain as an active ingredient a compound of formula (I) as defined hereinabove. Preferred compositions contain as active ingredient a novel compound of formula (I) while preferred methods of controlling weeds make use of the novel compounds.

In the method for controlling weeds according to the invention the compounds of formula (I) are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared by known means, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or expoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active-compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, synthetic surfactants are used, especially fatty sulfonates, fatty sulfates, sulfonated benzimidazole derivatives or alkylarylsulfonates.

The fatty sulfonates or sulfates usually occur as alkali metal salts, earth alkaline metal salts or unsubstitued or substituted ammonium salts and contain an alkyl radical consisting of 8 to 22 carbon atoms, said alkyl also comprising radicals derived from acyl groups of fatty acids, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substitutent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich and Vienna, 1981, M. and J. Ash, "Encyclopedia of Surfactants", Vol. I-III, Chemical Publishing Co., New York, 1980–81.

The herbidical compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 88 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85% |

Some of the compounds of the formula (1) which are used as active ingredients in the method for controlling weeds in accordance with the invention are listed in the following tables with the purpose of illustrating the invention and not limiting it thereto.

TABLE 1:

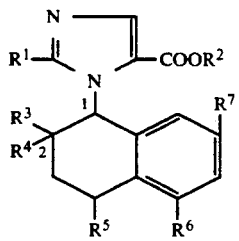

| Comp. No. | R¹ | R² | R³ | R⁴ | R⁵ | R⁶ | R⁷ | physical data |
|---|---|---|---|---|---|---|---|---|
| 1.01 | H | CH₃ | H | H | H | H | H | HNO₃/mp. 149-151.5° C. (dec.) |
| 1.02 | H | CH₃ | H | H | H | H | H | mp. 63° C. |
| 1.03 | H | CH₃ | CH₃ | CH₃ | H | H | H | mp. 100-101° C. |
| 1.04 | H | CH₃ | H | H | CH₃ | H | H | mp. 117-118° C. |
| 1.05 | H | CH₃ | H | H | H | H | OCH₃ | resin |
| 1.06 | H | CH₃ | H | H | H | CH₃ | CH₃ | HNO₃/mp. 136° C. (dec.) |
| 1.07 | H | CH₃ | H | H | H | OCH₃ | H | mp. 139-140° C. |
| 1.08 | H | CH₃ | CH₃ | CH₃ | H | H | H | HNO₃/mp. 160° C. (dec.) |
| 1.09 | H | CH₃ | H | H | H | CH₃ | CH₃ | resin |
| 1.10 | H | CH₃ | H | H | H | H | F | HNO₃/mp. 161° C. |
| 1.11 | SH | CH₃ | H | H | CH₃ | H | H | mp. 171-172° C. |
| 1.12 | SH | CH₃ | CH₃ | CH₃ | H | H | H | mp. 154-155° C. |
| 1.13 | SH | CH₃ | H | H | H | H | OCH₃ | mp. 184-186° C. |
| 1.14 | SH | CH₃ | H | H | H | CH₃ | CH₃ | mp. 190-190.5° C. |
| 1.15 | SH | CH₃ | H | H | H | OCH₃ | H | mp. 170-171° C. |
| 1.16 | SH | CH₃ | H | H | H | H | H | mp. 157-158° C. |
| 1.17 | SH | CH₃ | CH₃ | CH₃ | H | H | H | mp. 171-172° C. |
| 1.18 | H | C₂H₅ | H | H | H | H | H | HNO₃/mp. 135-136° C. |
| 1.19 | H | C₃H₇-n | H | H | H | H | H | HNO₃/mp. 109-110° C. |
| 1.20 | H | C₂H₅ | CH₃ | H | H | H | H | |
| 1.21 | H | CH₃ | H | H | OCH₃ | H | H | |
| 1.22 | H | CH₃ | H | H | H | OCH₃ | OCH₃ | |
| 1.23 | H | C₂H₅ | H | H | H | CH₃ | CH₃ | |
| 1.24 | H | C₃H₇-i | H | H | H | OCH₃ | H | |
| 1.25 | H | CH₃ | CH₃ | H | H | CH₃ | H | |
| 1.26 | H | C₃H₇-n | H | H | H | CH₃ | CH₃ | |
| 1.27 | H | C₂H₅ | H | H | H | H | F | |
| 1.28 | SH | C₂H₅ | H | H | CH₃ | H | H | |
| 1.29 | SH | C₂H₅ | CH₃ | H | H | H | H | |
| 1.30 | SH | CH₃ | H | H | H | OCH₃ | OCH₃ | |
| 1.31 | SH | C₂H₅ | H | H | H | CH₃ | CH₃ | |
| 1.32 | SH | C₃H₇-i | H | H | H | OCH₃ | H | |
| 1.33 | SH | C₃H₇-n | H | H | H | H | H | |
| 1.34 | SH | CH₃ | CH₃ | CH₃ | H | CH₃ | H | |
| 1.35 | H | C₆H₁₁-c | H | H | H | H | H | HNO₃/mp. 144-145° C. |
| 1.36 | SH | C₅H₉-c | H | H | H | H | H | |
| 1.37 | H | C₅H₉-c | CH₃ | CH₃ | H | H | H | |
| 1.38 | H | CH₃ | H | H | H | Cl | Cl | |
| 1.39 | SH | C₂H₅ | H | H | H | Cl | Cl | |
| 1.40 | SH | H | H | H | H | H | H | |
| 1.41 | H | H | H | H | H | H | H | mp. 206.5-210° C. |
| 1.42 | H | C₃H₇-i | H | H | H | H | H | HNO₃/mp. 138-140° C. |
| 1.43 | H | C₇H₁₅-n | H | H | H | H | H | |
| 1.44 | SH | CH₃ | H | H | H | H | F | mp. 205° C. |
| 1.45 | H | CH₃ | H | H | H | H | F | HNO₃/mp. 161° C. |
| 1.46 | SH | CH₃ | H | H | H | H | Br | mp. 206° C. |
| 1.47 | H | CH₃ | H | H | H | H | Br | HNO₃/mp. 172° C. |
| 1.48 | SH | CH₃ | H | H | H | H | Cl | mp. 218° C. |
| 1.49 | H | CH₃ | H | H | H | H | Cl | mp. 131° C. |
| 1.50 | SH | CH₃ | H | H | H | H | H | mp. 149-150° C. |
| 1.51 | H | CH₃ | H | H | H | H | H | (COOH)₂/mp. 136-138.5° C. |
| 1.52 | H | CH₂—CH=CH₂ | H | H | H | H | H | HNO₃/mp. 103-104° C. |
| 1.53 | H | C₄H₉-n | H | H | H | H | H | HNO₃/mp. 126-127° C. |
| 1.54 | H | C₅H₁₁-n | H | H | H | H | H | HNO₃/mp. 102-103.5° C. |
| 1.55 | H | (CH₃)₂CH\|CH₂— | H | H | H | H | H | HNO₃/mp. 139-140° C. |
| 1.56 | H | C₂H₅ | H | H | H | H | H | HNO₃/mp. 91-92.5° C. |

TABLE 1:-continued

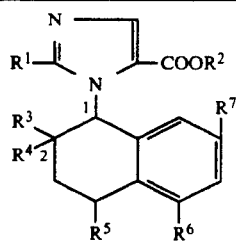

| Comp. No. | R¹ | R² | R³ | R⁴ | R⁵ | R⁶ | R⁷ | physical data |
|---|---|---|---|---|---|---|---|---|
| 1.57 | H | (CH₃)₂CH—CH(CH₂)—CH₃ (H₃C—CH—) | H | H | H | H | H | HNO₃/mp. 133.5–136° C. |
| 1.58 | H | CH₃ | CH₃ | H | H | H | H | HNO₃ |
| 1.59 | H | CH₃ | CH₃ | H | H | H | H | mp. 90–91° C. |
| 1.60 | H | C₃H₇-i | CH₃ | CH₃ | H | H | H | resin |
| 1.61 | H | C₂H₅ | CH₃ | CH₃ | H | H | H | mp. 74–75° C. |
| 1.62 | H | C₄H₉-n | CH₃ | CH₃ | H | H | H | mp. 64.5–66.5° C. |
| 1.63 | H | C₅H₁₁-n | CH₃ | CH₃ | H | H | H | mp. 72–75° C. |
| 1.64 | H | CH₃ | CH₃ | CH₃ | H | H | OCH₃ | HNO₃/mp. 163° C. (dec.) |
| 1.65 | H | CH₃ | CH₃ | CH₃ | H | H | OCH₃ | resin |
| 1.66 | H | CH₃ | CH₃ | CH₃ | H | CH₃ | CH₃ | HNO₃/mp. 163° C. (dec.) |
| 1.67 | H | CH₃ | CH₃ | CH₃ | H | CH₃ | CH₃ | mp. 133–134° C. |
| 1.68 | SH | CH₃ | CH₃ | CH₃ | H | CH₃ | CH₃ | mp. 200–201° C. |
| 1.69 | SH | CH₃ | CH₃ | CH₃ | H | H | OCH₃ | mp. 166–167° C. |
| 1.70 | H | H | CH₃ | CH₃ | H | H | H | mp. 238° C. |
| 1.71 | H | CH₃ | CH₃ | CH₃ | H | H | H | CH₃—SO₃H/mp. 141–151° C. |
| 1.72 | H | CH₃ | CH₃ | CH₃ | H | H | H | HBr/mp. 146° C. (dec.) |
| 1.73 | H | CH₃ | H | H | H | H | H | HBr/mp. 145° C. (dec.) |
| 1.74 | H | CH₃ | H | H | H | H | H | CH₃—C₆H₄—SO₃H/mp. 178–179° C. |
| 1.75 | H | CH₃ | CH₃ | CH₃ | H | H | H | HCl/mp. 158° C. (dec.) |
| 1.76 | H | CH₃ | CH₃ | CH₃ | H | H | H | CF₃COOH/mp. 92–93° C. |
| 1.77 | H | Na⁺ | H | H | H | H | H | |
| 1.78 | H | K⁺ | H | H | H | H | H | |
| 1.79 | H | NH₄⁺ | H | H | H | H | H | |
| 1.80 | H | C₄H₉-n | H | H | H | H | H | resin |
| 1.81 | H | C₃H₇-n | H | H | H | H | H | mp. 60–63° C. |
| 1.82 | H | C₆H₁₁-c | H | H | H | H | H | mp. 86–88° C. |
| 1.83 | H | CH₂—CH₂—OCH₃ | H | H | H | H | H | mp. 66.8° C. |
| 1.84 | H | CH₂—C≡CH | H | H | H | H | H | mp. 101–103° C. |
| 1.85 | H | CH₂—CH=CH₂ | H | H | H | H | H | mp. 81–82° C. |
| 1.86 | H | benzyl | H | H | H | H | H | HNO₃/mp. 133.5–134.5° C. |
| 1.87 | H | CH₃ | C₂H₅ | H | H | H | H | cis/resin |
| 1.88 | H | CH₃ | C₂H₅ | H | H | H | H | mp. 83–95° C./trans |
| 1.89 | SH | CH₃ | C₂H₅ | H | H | H | H | mp. 118–120° C. |
| 1.90 | H | CH₃ | C₃H₇-i | H | H | H | H | NHO₃ |
| 1.91 | H | CH₃ | C₃H₇-i | H | H | H | H | mp. 123–124.5° C. |
| 1.92 | SH | CH₃ | C₃H₇-i | H | H | H | H | mp. 174–175° C. |
| 1.93 | H | CH₃ | C₂H₅ | C₂H₅ | H | H | H | HNO₃/mp. 150–151° C. |
| 1.94 | H | CH₃ | C₂H₅ | C₂H₅ | H | H | H | mp. 109–110° C. |
| 1.95 | SH | CH₃ | C₂H₅ | C₂H₅ | H | H | H | mp. 164.5–165° C. |
| 1.96 | H | C₂H₅ | H | H | H | H | H | resin |
| 1.97 | H | C₃H₇-i | H | H | H | H | H | mp. 77–79° C. |
| 1.98 | H | C₆H₁₁-c | CH₃ | H | H | H | H | |
| 1.99 | SH | C₂H₅ | C₂H₅ | C₂H₅ | H | H | H | |
| 1.100 | H | C₂H₅ | C₂H₅ | C₂H₅ | H | H | H | |
| 1.101 | H | CH₃ | benzyl | H | H | H | H | trans/oil |
| 1.102 | H | C₅H₉-c | H | H | H | H | H | resin |
| 1.103 | H | CH₃ | C₃H₇-n | H | H | H | H | HNO₃/mp. 137° C. (dec.) |
| 1.104 | SH | CH₃ | C₃H₇-n | H | H | H | H | mp. 160–161° C. |
| 1.105 | H | CH₃ | C₄H₉-n | H | H | H | H | resin |
| 1.106 | SH | CH₃ | C₄H₉-n | H | H | H | H | mp. 139–140° C. |
| 1.107 | H | CH₃ | C₅H₁₁-n | H | H | H | H | 1,2-trans/mp. 79.5–80° C. |
| 1.108 | SH | CH₃ | C₅H₁₁-n | H | H | H | H | 1,2-trans/mp. 170–172° C. |
| 1.109 | H | CH₃ | H | H | H | NO₂ | H | mp. 148–152° C. |
| 1.110 | H | CH₃ | H | H | H | H | NO₂ | |
| 1.111 | H | CH₃ | CH₃ | CH₃ | H | NO₂ | H | |
| 1.112 | H | CH₃ | CH₃ | CH₃ | H | H | NO₂ | |

TABLE 1:-continued

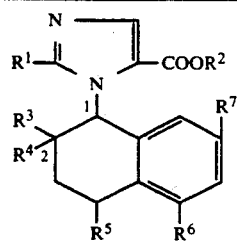

| Comp. No. | R¹ | R² | R³ | R⁴ | R⁵ | R⁶ | R⁷ | physical data |
|---|---|---|---|---|---|---|---|---|
| 1.113 | H | CH₃ | H | H | H | NH₂ | H | |
| 1.114 | H | CH₃ | H | H | H | H | NH₂ | |
| 1.115 | H | CH₃ | H | H | H | NHCOCH₃ | H | |
| 1.116 | H | CH₃ | H | H | H | H | NHCOCH₃ | |
| 1.117 | H | CH₃ | CH₃ | CH₃ | H | NH₂ | H | |
| 1.118 | H | CH₃ | CH₃ | CH₃ | H | H | NH₂ | |
| 1.119 | H | CH₃ | CH₃ | CH₃ | H | NHCOCH₃ | H | |
| 1.120 | H | CH₃ | CH₃ | CH₃ | H | H | NHCOCH₃ | |
| 1.121 | H | CH₃ | H | H | H | H | CF₃ | |
| 1.122 | H | CH₃ | H | H | H | H | OCHF₂ | |
| 1.123 | H | CH₃ | CH(C₆H₅)₂ | H | H | H | H | |
| 1.124 | SH | CH₃ | CH₃ | H | H | H | H | 1,2-cis |
| 1.125 | H | CH₃ | CH₃ | H | H | H | H | 1,2-cis/mp. 101-102° C. |
| 1.126 | SH | CH₃ | CH₃ | H | H | H | H | 1,2-trans/mp. 156-157° C. |
| 1.127 | H | CH₃ | CH₃ | H | H | H | H | 1,2-trans/mp. 110-110.5° C. |
| 1.128 | H | (CH₂)₂—OCH₃ | H | H | H | H | H | HNO₃/mp. 115-117° C. |
| 1.129 | H | (CH₂)₂—OC₂H₅ | H | H | H | H | H | HNO₃/mp. 117-118° C. |
| 1.130 | SH | C₂H₅ | H | H | H | H | H | HNO₃/mp. 155.5-157° C. |
| 1.131 | H | CH₃ | CH₃ | CH₃ | H | H | F | |
| 1.132 | SH | CH₃ | CH₃ | CH₃ | H | H | F | |
| 1.133 | H | CH₃ | CH₃ | CH₃ | H | H | Cl | |
| 1.134 | SH | CH₃ | CH₃ | CH₃ | H | H | Cl | |
| 1.135 | H | CH₃ | CH₃ | CH₃ | H | H | Br | |
| 1.136 | SH | CH₃ | CH₃ | CH₃ | H | H | Br | |
| 1.137 | SH | CH₃ | CH(C₆H₅)₂ | H | H | H | H | |
| 1.138 | SH | CH₃ | CH₂—CH=CH₂ | H | H | H | H | |
| 1.139 | H | CH₃ | CH₂—CH=CH₂ | H | H | H | H | |
| 1.140 | SH | CH₃ | CH₃ | C₂H₅ | H | H | H | resin |
| 1.141 | H | CH₃ | CH₃ | C₂H₅ | H | H | H | resin |
| 1.142 | SH | H | CH₃ | CH₃ | H | H | H | mp. 196-198° C. |
| 1.143 | H | H | CH₃ | CH₃ | H | H | H | |
| 1.144 | H | H | H | H | H | F | H | H₂O/mp. 129.9° C. |
| 1.145 | SH | H | H | H | H | F | H | |
| 1.146 | H | H | H | H | H | Cl | H | |
| 1.147 | SH | H | H | H | H | Cl | H | |
| 1.148 | H | H | H | H | H | Br | H | |
| 1.149 | SH | H | H | H | H | Br | H | |
| 1.150 | H | H | CH₃ | CH₃ | H | F | H | |
| 1.151 | H | H | CH₃ | CH₃ | H | Cl | H | |
| 1.152 | H | H | CH₃ | CH₃ | H | OCH₃ | H | |
| 1.153 | H | H | H | H | H | OCH₃ | H | |
| 1.154 | H | Na⁺ | CH₃ | CH₃ | H | H | H | |
| 1.155 | H | K⁺ | CH₃ | CH₃ | H | H | H | |
| 1.156 | H | NH₄⁺ | CH₃ | CH₃ | H | H | H | |
| 1.157 | H | N(CH₃)₄⁺ | CH₃ | CH₃ | H | H | H | |
| 1.158 | H | N(CH₃)₄⁺ | H | H | H | H | H | |
| 1.159 | SH | CH₃ | benzyl | H | H | H | H | 1,2-trans/mp. 210.3° C. |
| 1.160 | SH | CH₃ | benzyl | H | H | H | H | 1,2-cis/mp. 180.2° C. |
| 1.161 | H | CH₃ | benzyl | H | H | H | H | 1,2-trans/oil |
| 1.162 | H | CH₃ | benzyl | H | H | H | H | 1,2-cis/mp. 129.1° C. |
| 1.163 | H | CH₃ | benzyl | H | H | H | H | 1,2-trans/HNO₃ mp. 126.5° C. |
| 1.164 | H | CH₃ | benzyl | H | H | H | H | 1,2-cis/HNO₃ mp. 201.3° C. |
| 1.165 | SH | CH₃ | benzyl | H | H | H | H | |
| 1.166 | H | CH₃ | benzyl | H | H | H | H | HNO₃/mp. 144.3° C. |
| 1.167 | H | CH₃ | C₃H₇-n | H | H | H | H | resin |
| 1.168 | H | CH₃ | C₄H₉-n | H | H | H | H | 1,2-trans/mp. 90-90.5° C. |
| 1.169 | SH | CH₃ | C₅H₁₁-n | H | H | H | H | 1,2-cis/mp. 170-172° C. |
| 1.170 | H | CH₃ | C₅H₁₁-n | H | H | H | H | 1,2-cis |
| 1.171 | H | CH₃ | C₃H₇-n | H | H | H | H | HNO₃ |
| 1.172 | H | CH₃ | C₃H₇-n | H | H | H | H | 1,2-trans |
| 1.173 | H | CH₃ | C₃H₇-n | H | H | H | H | 1,2-cis |
| 1.174 | H | CH₃ | C₄H₉-n | H | H | H | H | HNO₃ |
| 1.175 | H | CH₃ | C₄H₉-n | H | H | H | H | 1,2-cis/resin |
| 1.176 | H | CH₂—C₆H₅ | H | H | H | H | H | |
| 1.177 | H | CH₃ | CH₃ | CH₃ | Cl | H | H | cis/mp. 146-147° C. |
| 1.178 | H | CH₃ | CH₃ | CH₃ | Cl | H | H | trans/mp. 94-96° C. |
| 1.179 | H | CH₃ | H | H | H | H | H | CH₃SO₃H mp. 148-151° C. |
| 1.180 | H | CH₃ | CH₃ | CH₃ | H | H | H | CH₃COOH/mp. 48-52° C. |

TABLE 1:-continued

| Comp. No. | R¹ | R² | R³ | R⁴ | R⁵ | R⁶ | R⁷ | physical data |
|---|---|---|---|---|---|---|---|---|
| 1.181 | H | $CH_3$ | $CH_3$ | $CH_3$ | H | H | H | $H_3C-C_6H_4-SO_3H$; mp. 159-160° C. |
| 1.182 | H | $CH_3$ | $CH_3$ | $CH_3$ | H | H | H | $CCl_3COOH$ |
| 1.183 | H | $CH_3$ | $CH_3$ | $CH_3$ | H | H | H | $H_2SO_4$ |
| 1.184 | H | $CH_3$ | $CH_3$ | $CH_3$ | H | H | H | $H_3PO_4$ |
| 1.185 | H | $CH_3$ | $CH_3$ | $CH_3$ | H | H | H | $H_3PO_3$ |
| 1.186 | H | $CH_3$ | $CH_3$ | $CH_3$ | H | H | H | $H_3PO_2$ |
| 1.187 | H | $CH_3$ | $CH_3$ | $CH_3$ | H | H | H | $(COOH)_2$ |
| 1.188 | H | $CH_3$ | $CH_3$ | $CH_3$ | H | H | H | $HOOC-(CH_2)_2-COOH$ |
| 1.189 | H | $CH_3$ | $CH_3$ | $CH_3$ | H | H | H | $H_3BO_3$ |
| 1.190 | H | $CH_3$ | $CH_3$ | $CH_3$ | H | H | H | $CH_3P(O)(OH)H$ |
| 1.191 | H | $CH_3$ | $CH_3$ | $CH_3$ | H | H | H | $CH_3P(O)(OH)_2$ |
| 1.192 | H | H | $CH_3$ | $CH_3$ | H | H | H | morpholine (HN–O ring) |
| 1.193 | H | Na | $CH_3$ | $CH_3$ | H | H |  | N,N-dimethylpiperidinium iodide |
| 1.194 | H | Na | $CH_3$ | $CH_3$ | H | H |  | N,N-dimethylmorpholinium iodide |
| 1.195 | H | Na | $CH_3$ | $CH_3$ | H | H |  | $ClCH_2N^+(CH_3)_3Cl^-$ |
| 1.196 | H | Na | $CH_3$ | $CH_3$ | H | H |  | $CH_3CH_2OOC-CH_2-NH_3^+Cl^-$ |
| 1.197 | H | H | $CH_3$ | $CH_3$ | H | H |  | 2,6-dimethylmorpholine |
| 1.198 | H | H | $CH_3$ | $CH_3$ | H | H |  | $CH_3-CH_2-NH-CH_2CH_3$ |
| 1.199 | H | H | $CH_3$ | $CH_3$ | H | H |  | $[(CH_3)_2CH]_2NH$ |
| 1.200 | H | H | $CH_3$ | $CH_3$ | H | H |  | piperidine (HN ring) |
| 1.201 | H | H | $CH_3$ | $CH_3$ | H | H |  | $HN(CH_2-CH_2OH)_2$ |
| 1.202 | H | H | $CH_3$ | $CH_3$ | H | H |  | $H_2N-CH_2-CH_2OH$ |
| 1.203 | H | H | $CH_3$ | $CH_3$ | H | H |  | $Cl-C_6H_4-CH_2-NH_2$ |

TABLE 1:-continued

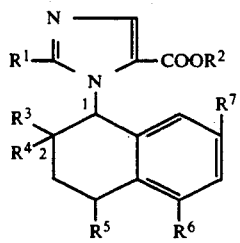

| Comp. No. | R¹ | R² | R³ | R⁴ | R⁵ | R⁶ | R⁷ | physical data |
|---|---|---|---|---|---|---|---|---|
| 1.204 | H | H | $CH_3$ | $CH_3$ | H | H | 2-Cl-C₆H₄-CH₂-NH₂ | |
| 1.205 | H | H | $CH_3$ | $CH_3$ | H | H | $H_2N-CH_2P(O)(OC_3H_7\text{-}i)_2$ | |
| 1.206 | H | $CH_3$ | $CH_3$ | $CH_3$ | H | H | (+)-(S) | |

TABLE 2

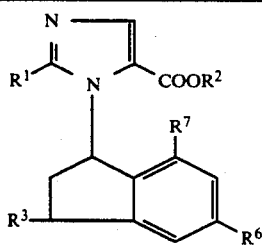

| Comp. No. | R¹ | R² | R³ | R⁶ | R⁷ | physical data |
|---|---|---|---|---|---|---|
| 2.01 | H | $CH_3$ | H | H | F | |
| 2.02 | H | $CH_3$ | H | H | Cl | |
| 2.03 | H | $CH_3$ | H | H | Br | |
| 2.04 | H | $CH_3$ | $CH_3$ | Cl | Cl | |
| 2.05 | SH | $CH_3$ | H | H | F | |
| 2.06 | SH | $C_2H_5$ | H | H | F | |
| 2.07 | SH | $CH_3$ | H | H | Cl | |
| 2.08 | SH | $CH_3$ | H | Cl | Cl | |
| 2.09 | H | $C_2H_5$ | H | Cl | Cl | |
| 2.10 | SH | $CH_3$ | $CH_3$ | Cl | Cl | |
| 2.11 | H | $C_2H_5$ | $C_2H_5$ | H | H | |
| 2.12 | SH | $C_2H_5$ | $C_2H_5$ | H | H | |
| 2.13 | H | $C_3H_7$-n | $CH_3$ | H | H | |
| 2.14 | SH | $C_3H_7$-n | $C_3H_7$-n | H | H | |
| 2.15 | H | $C_3H_7$-n | $C_3H_7$-n | H | H | |
| 2.16 | SH | $CH_3$ | H | H | $OCH_3$ | |
| 2.17 | H | $CH_3$ | H | H | $OCH_3$ | |
| 2.18 | SH | $CH_3$ | H | $CH_3$ | H | |
| 2.19 | H | $CH_3$ | H | $CH_3$ | H | mp. 66–69° C. |
| 2.20 | H | $CH_3$ | H | H | H | $HNO_3$/mp. 139.5–140.5° C. |
| 2.21 | H | $CH_3$ | H | H | H | mp. 82–83° C. |
| 2.22 | H | $C_2H_5$ | H | H | H | $HNO_3$/mp. 139–140° C. |
| 2.23 | H | $C_2H_5$ | H | H | H | mp. 139–140° C. |
| 2.24 | SH | $CH_3$ | H | F | H | mp. 191° C. |
| 2.25 | H | $CH_3$ | H | F | H | $HNO_3$/mp. 187° C. |
| 2.26 | SH | $CH_3$ | H | Cl | H | mp. 218° C. |
| 2.27 | H | $CH_3$ | H | Cl | H | $HNO_3$/mp. 214° C. |
| 2.28 | H | $CH_3$ | H | Br | H | $HNO_3$/mp. 164° C. |
| 2.29 | SH | $CH_3$ | $CH_3$ | Cl | Cl | mp. 203° C. |
| 2.30 | H | $CH_3$ | $CH_3$ | Cl | Cl | $HNO_3$/mp. 126° C. |
| 2.31 | SH | $CH_3$ | H | Br | H | solid |
| 2.32 | SH | $CH_3$ | H | H | H | mp. 158–160.5° C. |
| 2.33 | H | H | H | H | H | mp. 209–211.5° C. |
| 2.34 | SH | $CH_3$ | $CH_3$ | H | H | mp. 176.6° C. |
| 2.35 | H | $CH_3$ | $CH_3$ | H | H | $HNO_3$/mp. 140.3° C. |
| 2.36 | H | H | $CH_3$ | H | H | mp. 209.3° C. |
| 2.37 | H | $CH_3$ | H | H | $CH_3$ | mp. 77–80° C. |

TABLE 3

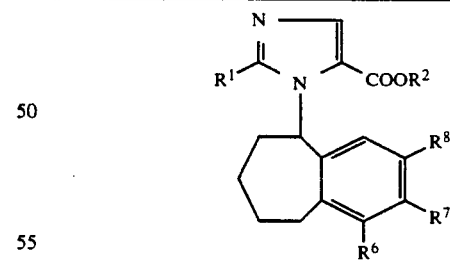

| Comp. No. | R¹ | R² | R⁶ | R⁷ | R⁸ | physical data |
|---|---|---|---|---|---|---|
| 3.01 | SH | $CH_3$ | H | H | H | mp. 230° C. (dec.) |
| 3.02 | H | $CH_3$ | H | H | H | $HNO_3$/mp. 141–144° C. |
| 3.03 | H | $C_2H_5$ | H | H | H | |
| 3.04 | H | $CH_3$ | Cl | H | Cl | |
| 3.05 | H | $CH_3$ | H | Cl | Cl | |
| 3.06 | SH | $C_2H_5$ | H | H | H | |
| 3.07 | SH | $CH_3$ | Cl | H | Cl | |
| 3.08 | SH | $CH_3$ | H | Cl | Cl | |
| 3.09 | H | $CH_3$ | H | H | F | |
| 3.10 | SH | $CH_3$ | H | H | F | |
| 3.11 | SH | $CH_3$ | $OCH_3$ | $CH_3$ | H | |
| 3.12 | H | $CH_3$ | $OCH_3$ | $CH_3$ | H | |

| | | | | | |
|---|---|---|---|---|---|
| 3.13 | SH | CH₃ | H | H | CH₃ |
| 3.14 | H | CH₃ | H | H | CH₃ |

TABLE 3-continued

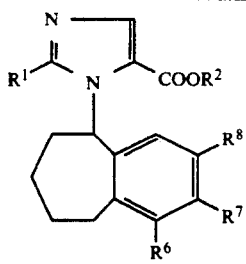

| Comp. No. | R¹ | R² | R⁶ | R⁷ | R⁸ | physical data |
|---|---|---|---|---|---|---|

TABLE 4

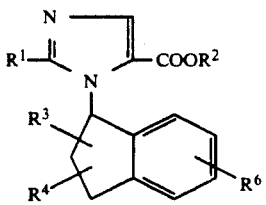

| Comp. No. | R¹ | R² | R³ | R⁴ | R⁶ | physical data |
|---|---|---|---|---|---|---|
| 4.01 | SH | CH₃ | 2-CH₃ | 2-CH₃ | H | mp. 171–172° C. |
| 4.02 | H | CH₃ | 2-CH₃ | 2-CH₃ | H | HNO₃/mp. 172–173° C. |
| 4.03 | H | CH₃ | 2-CH₃ | 2-CH₃ | H | mp. 96.5–97.5° C. |
| 4.04 | SH | CH₃ | 2-C₂H₅ | 2-C₂H₅ | H | mp. 164–165° C. |
| 4.05 | H | CH₃ | 2-C₂H₅ | 2-C₂H₅ | H | HNO₃ |
| 4.06 | H | CH₃ | 2-C₂H₅ | 2-C₂H₅ | H | mp. 83.5–85° C. |
| 4.07 | SH | CH₃ | 2-C₃H₇-i | H | H | |
| 4.08 | H | CH₃ | 2-C₃H₇-i | H | H | bp. 150–155° C. at 1 Pa |
| 4.09 | H | CH₃ | 2-C₃H₇-i | H | H | HNO₃ |
| 4.10 | SH | CH₃ | 2-CH₃ | H | 5-Cl | |
| 4.11 | H | CH₃ | 2-CH₃ | H | 5-Cl | $n_D^{30}$ = 1.560 cis/trans 4/1 |
| 4.12 | SH | CH₃ | 2-C₃H₇-n | H | H | |
| 4.13 | H | CH₃ | 2-C₃H₇-n | H | H | |
| 4.14 | SH | CH₃ | 2-C₄H₉-n | H | H | |
| 4.15 | H | CH₃ | 2-C₄H₉-n | H | H | |
| 4.16 | SH | CH₃ | 2-benzyl | H | H | solid |
| 4.17 | H | CH₃ | 2-benzyl | H | H | |
| 4.18 | SH | CH₃ | 2-C₅H₁₁-n | H | H | |
| 4.19 | H | CH₃ | 2-C₅H₁₁-n | H | H | |
| 4.20 | SH | CH₃ | 2-CH₃ | H | H | mp. 155–157° C. |
| 4.21 | H | CH₃ | 2-CH₃ | H | H | HNO₃/mp. 137–138° C. cis/trans (1/4) |
| 4.22 | SH | CH₃ | 2-C₂H₅ | H | H | |
| 4.23 | H | CH₃ | 2-C₂H₅ | H | H | |
| 4.24 | H | H | 2-CH₃ | 2-CH₃ | H | mp. 208–209° C. (dec.) |
| 4.25 | SH | CH₃ | 2-CH₃ | 2-CH₃ | 6-CH₃ | |
| 4.26 | H | CH₃ | 2-CH₃ | 2-CH₃ | 6-CH₃ | liquid |
| 4.27 | SH | CH₃ | 2-CH₃ | 2-CH₃ | 6-Cl | |
| 4.28 | H | CH₃ | 2-CH₃ | 2-CH₃ | 6-Cl | mp. 156–158° C. |
| 4.29 | SH | CH₃ | 2-CH₃ | 2-CH₃ | 6-F | |
| 4.30 | H | CH₃ | 2-CH₃ | 2-CH₃ | 6-F | |
| 4.31 | SH | CH₃ | 2-CH₃ | 2-CH₃ | 6-OCH₃ | |
| 4.32 | H | CH₃ | 2-CH₃ | 2-CH₃ | 6-OCH₃ | mp. 105–106° C. |
| 4.33 | SH | CH₃ | 2-CH₃ | 2-CH₃ | 5-CH₃ | |
| 4.34 | H | CH₃ | 2-CH₃ | 2-CH₃ | 5-CH₃ | $n_D^{30}$ = 1.5502 |
| 4.35 | H | C₂H₅ | 2-CH₃ | 2-CH₃ | H | mp. 124–125° C. |
| 4.36 | H | C₃H₇-n | 2-CH₃ | 2-CH₃ | H | mp. 90–91.5° C. |
| 4.37 | H | C₃H₇-i | 2-CH₃ | 2-CH₃ | H | mp. 140–141° C. |
| 4.38 | H | C₆H₁₃-n | 2-CH₃ | 2-CH₃ | H | |
| 4.39 | H | CH₂—CH=CH₂ | 2-CH₃ | 2-CH₃ | H | |
| 4.40 | H | CH₂—C≡CH | 2-CH₃ | 2-CH₃ | H | |
| 4.41 | H | CH₂—CH₂—OCH₃ | 2-CH₃ | 2-CH₃ | H | |
| 4.42 | SH | CH₃ | 2-CH₃ | H | H | HNO₃ |
| 4.43 | H | CH₃ | 2-CH₃ | H | H | trans/HNO₃/mp. 160–162° C. |
| 4.44 | H | CH₃ | 2-CH₃ | H | H | cis/resin |
| 4.45 | H | CH₃ | 2-CH₃ | H | H | cis/HNO₃/mp. 160–162° C. |
| 4.46 | SH | CH₃ | 2-CH₃ | 2-benzyl | H | trans/mp. 183–184° C. |
| 4.47 | H | CH₃ | 2-CH₃ | H | H | trans/resin |
| 4.48 | H | CH₃ | 2-CH₃ | 2-CH₃ | H | HCl/mp. 152–154° C. |
| 4.49 | H | CH₃ | 2-CH₃ | 2-CH₃ | H | CH₃SO₃H/193–195° C. |
| 4.50 | H | CH₃ | 2-CH₃ | 2-CH₃ | H | 4-CH₃—C₆H₄—SO₃H mp. 189–191° C. |
| 4.51 | SH | CH₃ | 2-CH₃ | 2-CH₃ | H | $[\alpha]_D^{20}$ = −140.5°/(S) mp. 115–118° C./mixture of atropisomers |
| 4.52 | SH | CH₃ | 2-CH₃ | 2-CH₃ | H | (R)/$[\alpha]_D^{20}$ = +144°/mp. 110–112° C./mixture of atropisomers |
| 4.53 | H | CH₃ | 2-CH₃ | 2-CH₃ | H | (S)/$[\alpha]_D^{20}$ = +76.3° |

TABLE 4-continued

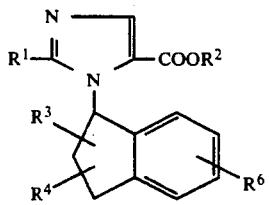

| Comp. No. | R¹ | R² | R³ | R⁴ | R⁶ | physical data |
|---|---|---|---|---|---|---|
| 4.54 | H | $CH_3$ | 2-$CH_3$ | 2-$CH_3$ | H | mp. 73-75° C. (R)/$[\alpha]_D^{20}$ = -72.9° |
| 4.55 | SH | $CH_3$ | 2-$CH_3$ | 2-$C_2H_5$ | H | mp. 73-75° C. |
| 4.56 | H | $CH_3$ | 2-$CH_3$ | 2-$C_2H_5$ | H | resin |
| 4.57 | H | $CH_3$ | 2-$CH_3$ | 2-$C_2H_5$ | H | $HNO_3$/mp. 137-139° C. |
| 4.58 | SH | $CH_3$ | 2-$CH_3$ | 2-benzyl | H | cis/mp. 225.5-226° C. (dec.) |
| 4.59 | H | $CH_3$ | 2-$CH_3$ | 2-benzyl | H | cis/mp. 152-153° C. |
| 4.60 | H | $CH_3$ | 2-$CH_3$ | 2-benzyl | H | trans/mp. 88.5-89.5° C. |
| 4.61 | SH | $CH_3$ | 2-benzyl | 2-benzyl | H | |
| 4.62 | H | $CH_3$ | 2-benzyl | 2-benzyl | H | |
| 4.63 | H | $CH_3$ | 2-benzyl | 2-benzyl | H | $HNO_3$ |
| 4.64 | H | $C_4H_9$-n | 2-$CH_3$ | 2-$CH_3$ | H | resin |
| 4.65 | SH | $CH_3$ | 3-$CH_3$ | 3-$CH_3$ | H | mp. 190.0° C. |
| 4.66 | H | $CH_3$ | 3-$CH_3$ | 3-$CH_3$ | H | $HNO_3$/mp. 152.4° C. |
| 4.67 | H | $CH_3$ | 3-$CH_3$ | 3-$CH_3$ | H | oil |
| 4.68 | H | H | 3-$CH_3$ | 3-$CH_3$ | H | mp. 180.0° C. |
| 4.69 | SH | $CH_3$ | 2-benzyl | H | H | $HNO_3$/trans |
| 4.70 | H | $CH_3$ | 2-benzyl | H | H | $HNO_3$/trans/mp. 142.8° C. |
| 4.71 | SH | $CH_3$ | 2-benzyl | H | H | $HNO_3$/cis |
| 4.72 | H | $CH_3$ | 2-benzyl | H | H | $HNO_3$/cis/mp. 133.7° C. |
| 4.73 | H | $CH_3$ | 2-$CH_3$ | H | 5-$OCH_3$ | cis/trans(2/5)/mp. 78-81° C. |
| 4.74 | H | $CH_3$ | 2-$CH_3$ | H | 5-F | cis/trans(4/1)/$n_D^{30}$ = 1.5412 |
| 4.75 | H | $CH_3$ | 2-$CH_3$ | H | 5-F | trans/$n_D^{30}$ = 1.5405 |
| 4.76 | H | $CH_3$ | 2-$CH_3$ | H | 6-Cl | cis/trans(1/4)/solid |
| 4.77 | H | $CH_3$ | 2-$CH_3$ | H | 7-F | cis/trans(1/1)/$n_D^{30}$ = 1.5410 |
| 4.78 | H | $CH_3$ | 2-(2,4-$Cl_2C_6H_3$) | H | H | bp. 180-185° C. at 2 Pa |
| 4.79 | SH | $CH_3$ | 2-$CH_3$ | 2-$CH_3$ | H | (R)-atropisomer A/ mp. 176-177° C./$[\alpha]_D^{20}$ = -16.9°* |
| 4.80 | SH | $CH_3$ | 2-$CH_3$ | 2-$CH_3$ | H | (R)-atropis. B/0.25 $C_6H_{12}$ mp. 75° C./$[\alpha]_D^{20}$ = +296°* |
| 4.81 | SH | $CH_3$ | 2-$CH_3$ | 2-$CH_3$ | H | (S)-atropis. A/mp. 175.5-176.5° C./$[\alpha]_D^{20}$ = +16.4°* |
| 4.82 | SH | $CH_3$ | 2-$CH_3$ | 2-$CH_3$ | H | (S)atropis. B/0.25 $C_6H_{12}$ mp. 75° C./$[\alpha]_D^{20}$ = -303°* |
| 4.83 | SH | $CH_3$ | 2-$CH_3$ | 2-$CH_3$ | H | (RS)-atropisomer/ mp. 142-143° C. |
| 4.84 | H | $CH_3$ | 2-$CH_3$ | 2-$CH_3$ | H | HBr |
| 4.85 | H | $CH_3$ | 2-$CH_3$ | 2-$CH_3$ | H | $CH_3COOH$ |
| 4.86 | H | $CH_3$ | 2-$CH_3$ | 2-$CH_3$ | H | $CF_3COOH$ |
| 4.87 | H | $CH_3$ | 2-$CH_3$ | 2-$CH_3$ | H | $CCl_3COOH$ |
| 4.88 | H | $CH_3$ | 2-$CH_3$ | 2-$CH_3$ | H | $H_2SO_4$ |
| 4.89 | H | $CH_3$ | 2-$CH_3$ | 2-$CH_3$ | H | $H_3PO_4$ |
| 4.90 | H | $CH_3$ | 2-$CH_3$ | 2-$CH_3$ | H | $H_3PO_3$ |
| 4.91 | H | $CH_3$ | 2-$CH_3$ | 2-$CH_3$ | H | $H_3PO_2$ |
| 4.92 | H | $CH_3$ | 2-$CH_3$ | 2-$CH_3$ | H | $(COOH)_2$ |
| 4.93 | H | $CH_3$ | 2-$CH_3$ | 2-$CH_3$ | H | $(CH_2COOH)_2$ |
| 4.94 | H | $CH_3$ | 2-$CH_3$ | 2-$CH_3$ | H | $H_3BO_3$ |
| 4.95 | H | $CH_3$ | 2-$CH_3$ | 2-$CH_3$ | H | $CH_3P(O)(OH)H$ |
| 4.96 | H | $CH_3$ | 2-$CH_3$ | 2-$CH_3$ | H | $CH_3P(O)(OH)_2$ |
| 4.97 | H | $CH_3$ | 2-$CH_3$ | 2-$CH_3$ | H | $HBF_4$ |
| 4.98 | H | $CH_3$ | 2-$CH_3$ | 2-$CH_3$ | H | $HPF_6$ |
| 4.99 | H | $C_4H_9$-n | 2-$CH_3$ | 2-$CH_3$ | H | $C_4H_9$—$OSO_3H$/mp. 130-131° C. |
| 4.100 | H | $CH_3$ | 2-$CH_3$ | 2-$CH_3$ | H | $HNO_3$/(R)/mp. 146.5-147.5° C. |
| 4.101 | H | $CH_3$ | 2-$CH_3$ | 2-$CH_3$ | H | HCl/(R) |
| 4.102 | H | $CH_3$ | 2-$CH_3$ | 2-$CH_3$ | 4-$CH_3$ | mp. 125-128° C. |
| 4.103 | H | $CH_3$ | 2-$CH_3$ | 2-$CH_3$ | 4-F | mp. 97-100° C. |
| 4.104 | H | $CH_3$ | 2-$CH_3$ | 2-$CH_3$ | 4-Cl | mp. 111-115° C. |
| 4.105 | H | $CH_3$ | 2-$CH_3$ | 2-$CH_3$ | 5-$OCH_3$ | $n_D^{30}$ = 1.5504 |
| 4.106 | H | $CH_3$ | 2-$CH_3$ | 2-$CH_3$ | 5-F | $n_D^{30}$ = 1.5385 |
| 4.107 | H | $CH_3$ | 2-$CH_3$ | 2-$CH_3$ | 5-Cl | mp. 88-90° C. |
| 4.108 | H | $CH_3$ | 2-$CH_3$ | 2-$CH_3$ | 5-Cl | $HNO_3$/mp. 200° C. |
| 4.109 | H | $CH_3$ | 2-$CH_3$ | 2-$CH_3$ | 5-$CF_3$ | |
| 4.110 | H | $CH_3$ | 2-$CH_3$ | 2-$CH_3$ | 7-$CH_3$ | mp. 95-98° C. |
| 4.111 | H | $CH_3$ | 2-$CH_3$ | 2-$CH_3$ | 7-F | mp. 95-98° C. |
| 4.112 | H | H | 2-$CH_3$ | 2-$CH_3$ | H | (R)/mp. 215° C. (dec.) $[\alpha]_D^{20}$ = -72° |
| 4.113 | H | H | 2-$CH_3$ | 2-$CH_3$ | H | $(HO—CH_2—CH_2)_2NH$ |
| 4.114 | H | H | 2-$CH_3$ | 2-$CH_3$ | H | $(CH_3—CH_2)_2NH$ |

TABLE 4-continued

| Comp. No. | R¹ | R² | R³ | R⁴ | R⁶ | physical data |
|---|---|---|---|---|---|---|
| 4.115 | H | H | 2-CH₃ | 2-CH₃ | H | 4-Cl—C₆H₄—CH₂—NH₂ |
| 4.116 | H | H | 2-CH₃ | 2-CH₃ | H | 2-Cl—C₆H₄—CH₂—NH₂ |
| 4.117 | H | H | 2-CH₃ | 2-CH₃ | H | HO—CH₂—CH₂—NH₂ |
| 4.118 | H | H | 2-CH₃ | 2-CH₃ | H | morpholine (O⌒NH) |
| 4.119 | H | H | 2-CH₃ | 2-CH₃ | H | 2,6-dimethylmorpholine |
| 4.120 | H | H | 2-CH₃ | 2-CH₃ | H | CH₃—CH₂OOC—CH₂—NH₂ |
| 4.121 | H | H | 2-CH₃ | 2-CH₃ | H | hexamethyleneimine (HN⌒) |
| 4.122 | H | H | 2-CH₃ | 2-CH₃ | H | (i-C₃H₇O)₂P(O)—CH₂—NH₂ |
| 4.123 | H | Na | 2-CH₃ | 2-CH₃ | H | |
| 4.124 | H | Na | 2-CH₃ | 2-CH₃ | H | N,N-dimethylpiperidinium iodide |
| 4.125 | H | Na | 2-CH₃ | 2-CH₃ | H | N,N-dimethylmorpholinium iodide |
| 4.126 | H | Na | 2-CH₃ | 2-CH₃ | H | Cl—CH₂—CH₂—⁺N(CH₃)₃·Cl⁻ |
| 4.127 | H | K | 2-CH₃ | 2-CH₃ | H | |
| 4.128 | H | C₂H₅ | 2-CH₃ | 2-CH₃ | H | (R)/mp. 108.5–109.5° C. [α]$_D^{20}$ = −75° |
| 4.129 | H | CH₃ | 2-CH₃ | 2-C₂H₅ | H | cis/mp. 77.5–82° C. |
| 4.130 | H | CH₃ | 2-CH₃ | 2-C₂H₅ | H | trans/resin |
| 4.131 | SH | CH₃ | 2-CH₃ | 2-C₃H₇-n | H | resin |
| 4.132 | H | CH₃ | 2-CH₃ | 2-C₃H₇-n | H | mp. 150–153° C. |
| 4.133 | H | CH₃ | 2-CH₃ | 2-C₃H₇-n | H | cis/mp. 109–111° C. |
| 4.134 | SH | CH₃ | 2-CH₃ | 2-C₄H₉-n | H | mp. 109–120° C. |
| 4.135 | H | CH₃ | 2-CH₃ | 2-C₄H₉-n | H | trans/resin |
| 4.136 | SH | CH₃ | 2-C₂H₅ | 2-C₂H₅ | H | atropisomer/mp. 160–162° C. |
| 4.137 | H | H | 2-C₂H₅ | 2-C₂H₅ | H | mp. 215–217° C. |
| 4.138 | H | CH₃ | 2-CH₃ | 2-C₃H₇-i | 7-Cl | mp. 189–192° C. |
| 4.139 | H | CH₃ | 2-C₃H₇-n | 2-C₃H₇-n | H | oil |

*[α]$_D^{20}$ in trichloromethane

TABLE 5

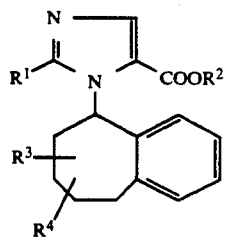

| Comp. No. | R¹ | R² | R³ | R⁴ | physical data |
|---|---|---|---|---|---|
| 5.01 | SH | CH₃ | H | H | |
| 5.02 | H | CH₃ | H | H | |
| 5.03 | H | benzyl | H | H | |
| 5.04 | SH | benzyl | H | H | |
| 5.05 | H | CH₃ | 2-CH₃ | 2-CH₃ | HNO₃/mp. 135.6° C. (dec.) |
| 5.06 | SH | CH₃ | 2-CH₃ | 2-CH₃ | mp. 209–209.5° C. |
| 5.07 | H | C₂H₅ | 2-CH₃ | 2-CH₃ | |
| 5.08 | SH | C₂H₅ | 2-CH₃ | 2-CH₃ | |

TABLE 6

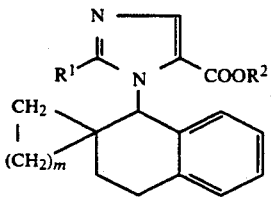

| Comp. No. | R¹ | R² | m | physical data |
|---|---|---|---|---|
| 6.01 | SH | CH₃ | 3 | mp. 161–164° C. |
| 6.02 | H | CH₃ | 3 | HNO₃/mp. 132° C. (dec.) |
| 6.03 | H | CH₃ | 3 | mp. 153–154° C. |
| 6.04 | SH | CH₃ | 4 | mp. 196–197° C. |
| 6.05 | H | CH₃ | 4 | mp. 177–178° C. |
| 6.06 | H | CH₃ | 4 | HNO₃/mp. 145.2° C. (dec.) |
| 6.07 | H | CH₂—CH=CH₂ | 3 | |
| 6.08 | SH | CH₂—CH=CH₂ | 3 | |
| 6.09 | H | CH₂—CH₂—OCH₃ | 4 | |
| 6.10 | SH | CH₂—CH₂—OCH₃ | 4 | |
| 6.11 | SH | CH₃ | 1 | |
| 6.12 | H | CH₃ | 1 | |
| 6.13 | SH | CH₃ | 2 | |
| 6.14 | H | CH₃ | 2 | |

TABLE 7

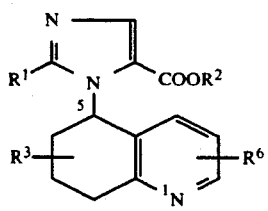

| Comp. No. | R¹ | R² | R³ | R⁶ | physical data |
|---|---|---|---|---|---|
| 7.01 | SH | CH₃ | H | 2-CH₃ | mp. 233° C. (dec.) |
| 7.02 | H | CH₃ | H | 2-CH₃ | |
| 7.03 | H | C₂H₅ | 6-CH₃ | H | |
| 7.04 | SH | C₂H₅ | 6-CH₃ | H | |
| 7.05 | H | CH₃ | 6-CH₃ | H | |
| 7.06 | SH | CH₃ | 6-CH₃ | H | |

TABLE 8

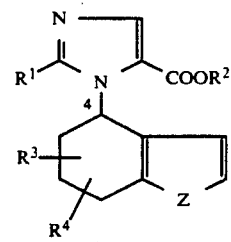

| Comp. No. | R¹ | R² | R³ | R⁴ | Z | physical data |
|---|---|---|---|---|---|---|
| 8.01 | SH | CH₃ | 6-CH₃ | 6-CH₃ | O | mp. 180–182° C. |
| 8.02 | SH | CH₃ | H | H | S | mp. 166° C. |
| 8.03 | H | CH₃ | H | H | S | HNO₃/mp. 154° C. |
| 8.04 | SH | CH₃ | 5-CH₃ | 5-CH₃ | S | |
| 8.05 | H | CH₃ | 5-CH₃ | 5-CH₃ | S | |
| 8.06 | H | CH₃ | 5-CH₃ | H | S | |
| 8.07 | SH | CH₃ | 5-CH₃ | H | S | |
| 8.08 | H | CH₃ | 5-C₂H₅ | H | S | |
| 8.09 | H | CH₃ | 5-C₃H₇-i | H | S | |
| 8.10 | H | CH₃ | 6-CH₃ | 6-CH₃ | O | |
| 8.11 | SH | CH₃ | H | H | O | |
| 8.12 | H | CH₃ | H | H | O | |
| 8.13 | SH | C₂H₅ | 5-CH₃ | 5-CH₃ | O | |
| 8.14 | H | C₂H₅ | 5-CH₃ | 5-CH₃ | O | |
| 8.15 | SH | C₅H₉-c | 5-CH₃ | H | S | |
| 8.16 | H | C₅H₉-c | 5-CH₃ | H | S | |
| 8.17 | H | H | H | H | S | HCl/mp. 223.5° C. |

TABLE 9

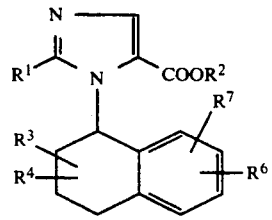

| Comp. No. | R¹ | R² | R³ | R⁴ | R⁶ | R⁷ | physical data |
|---|---|---|---|---|---|---|---|
| 9.01 | SH | CH₃ | 3-CH₃ | 3-CH₃ | H | H | |
| 9.02 | H | CH₃ | 3-CH₃ | 3-CH₃ | H | H | HNO₃ |
| 9.03 | H | CH₃ | 3-CH₃ | 3-CH₃ | H | H | |
| 9.04 | SH | CH₃ | 2-CH₃ | 3-CH₃ | H | H | |
| 9.05 | H | CH₃ | 2-CH₃ | 3-CH₃ | H | H | |
| 9.06 | H | CH₃ | 2-CH₃ | 3-CH₃ | H | H | HNO₃ |
| 9.07 | H | CH₃ | 2-CH₃ | 3-CH₃ | H | H | 2,3-cis |
| 9.08 | H | CH₃ | 2-CH₃ | 3-CH₃ | H | H | 2,3-trans |
| 9.09 | H | C₂H₅ | 3-CH₃ | H | 7-Br | H | |
| 9.10 | SH | C₂H₅ | 3-CH₃ | H | 7-Br | H | |
| 9.11 | H | CH₃ | 3-CH₃ | 3-CH₃ | 8-Cl | H | |
| 9.12 | SH | CH₃ | 3-CH₃ | 3-CH₃ | 8-Cl | H | |
| 9.13 | SH | CH₃ | H | H | 6-Cl | H | mp. 181° C. |
| 9.14 | H | CH₃ | H | H | 6-Cl | H | HNO₃/mp. 151° C. |
| 9.15 | SH | CH₃ | H | H | 6-Cl | 7-Cl | mp. 212° C. |
| 9.16 | H | CH₃ | H | H | 6-Cl | 7-Cl | HNO₃/mp. 200° C. |
| 9.17 | SH | CH₃ | 3-CH₃ | H | H | H | |
| 9.18 | H | CH₃ | 3-CH₃ | H | H | H | |
| 9.19 | SH | CH₃ | 3-C₂H₅ | H | H | H | |
| 9.20 | H | CH₃ | 3-C₂H₅ | H | H | H | |
| 9.21 | SH | CH₃ | 3-C₂H₅ | 3-C₂H₅ | H | H | |
| 9.22 | H | CH₃ | 3-C₂H₅ | 3-C₂H₅ | H | H | |
| 9.23 | H | H | H | H | 6-Cl | H | solid mp. 112–114° C. |
| 9.24 | H | CH₃ | 3-CH₃ | 3-CH₃ | 6-CH₃ | 8-CH₃ | |

TABLE 9-continued

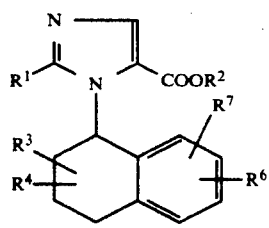

| Comp. No. | R¹ | R² | R³ | R⁴ | R⁶ | R⁷ | physical data |
|---|---|---|---|---|---|---|---|
| 9.25 | H | H | 3-CH₃ | 3-CH₃ | 6-CH₃ | 8-CH₃ | mp. 190–192° C. |

TABLE 10

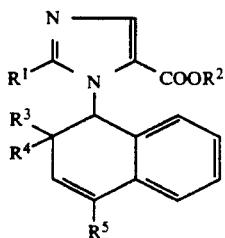

| Comp. No. | R¹ | R² | R³ | R⁴ | R⁵ | physical data |
|---|---|---|---|---|---|---|
| 10.01 | H | CH₃ | CH₃ | CH₃ | H | mp. 60–62° C. |
| 10.02 | SH | CH₃ | CH₃ | CH₃ | H | |
| 10.03 | SH | CH₃ | H | H | H | |
| 10.04 | H | CH₃ | H | H | H | |
| 10.05 | SH | CH₃ | CH₃ | H | H | |
| 10.06 | H | CH₃ | CH₃ | H | H | |
| 10.07 | SH | C₄H₉-n | H | H | H | |
| 10.08 | H | C₄H₉-n | H | H | H | |
| 10.09 | H | CH₃ | CH₃ | CH₃ | Br | mp. 101–103° C. |
| 10.10 | H | CH₃ | CH₃ | CH₃ | OCH₃ | mp. 102–104° C. |
| 10.11 | H | CH₃ | CH₃ | CH₃ | OC₂H₅ | wax. |

TABLE 11

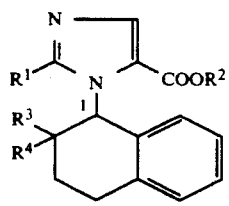

| Comp. No. | R¹ | R² | R³ | R⁴ | $[\alpha]_D^{20}$ | physical data |
|---|---|---|---|---|---|---|
| 11.01 | SH | CH₃ | H | H | +97.1° | mp. 141° C. |
| 11.02 | SH | CH₃ | H | H | −87.9° | mp. 141° C. |
| 11.03 | H | CH₃ | H | H | −25.8° | resin |
| 11.04 | H | CH₃ | H | H | +23.6° | resin |
| 11.05 | SH | CH₃ | CH₃ | CH₃ | + | |
| 11.06 | SH | CH₃ | CH₃ | CH₃ | − | |
| 11.07 | H | CH₃ | CH₃ | CH₃ | + | |
| 11.08 | H | CH₃ | CH₃ | CH₃ | − | |

TABLE 12

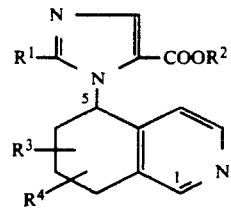

| Comp. No. | R¹ | R² | R³ | R⁴ |
|---|---|---|---|---|
| 12.01 | SH | CH₃ | H | H |
| 12.02 | H | CH₃ | H | H |
| 12.03 | SH | CH₃ | 6-CH₃ | H |
| 12.04 | H | CH₃ | 6-CH₃ | H |
| 12.05 | SH | CH₃ | 6-CH₃ | 6-CH₃ |
| 12.06 | H | CH₃ | 6-CH₃ | 6-CH₃ |
| 12.07 | SH | CH₃ | 6-C₃H₇-n | H |
| 12.08 | H | CH₃ | 6-C₃H₇-n | H |

TABLE 13

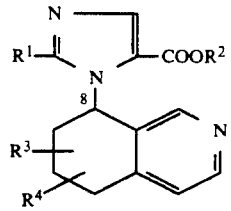

| Comp. No. | R¹ | R² | R³ | R⁴ |
|---|---|---|---|---|
| 13.01 | SH | CH₃ | H | H |
| 13.02 | H | CH₃ | H | H |
| 13.03 | SH | CH₃ | 7-CH₃ | H |
| 13.04 | H | CH₃ | 7-CH₃ | H |
| 13.05 | SH | CH₃ | 7-CH₃ | 7-CH₃ |
| 13.06 | H | CH₃ | 7-CH₃ | 7-CH₃ |
| 13.07 | H | CH₃ | 7-benzyl | H |
| 13.08 | SH | CH₃ | 7-benzyl | H |
| 13.09 | H | C₂H₅ | 7-allyl | H |
| 13.10 | SH | C₂H₅ | 7-allyl | H |

TABLE 14

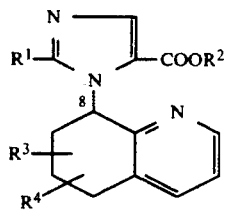

| Comp. No. | R¹ | R² | R³ | R⁴ |
|---|---|---|---|---|
| 14.01 | SH | CH₃ | H | H |
| 14.02 | H | CH₃ | H | H |
| 14.03 | SH | CH₃ | 7-CH₃ | H |
| 14.04 | H | CH₃ | 7-CH₃ | H |
| 14.05 | SH | CH₃ | 7-CH₃ | 7-CH₃ |
| 14.06 | H | CH₃ | 7-CH₃ | 7-CH₃ |
| 14.07 | SH | C₃H₇-i | H | H |
| 14.08 | H | C₃H₇-i | H | H |

TABLE 15

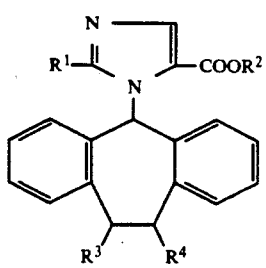

| Comp. No. | R¹ | R² | R³ | R⁴ |
|---|---|---|---|---|
| 15.01 | SH | $CH_3$ | H | H |
| 15.02 | H | $CH_3$ | H | H |
| 15.03 | H | $C_2H_5$ | H | H |
| 15.04 | H | $C_2H_5$ | $CH_3$ | H |
| 15.05 | H | $CH_3$ | $CH_3$ | $CH_3$ |
| 15.06 | H | $C_5H_{11}$-n | H | H |
| 15.07 | H | $C_6H_{11}$-c | H | H |
| 15.08 | H | $C_3H_7$-i | H | H |

TABLE 16

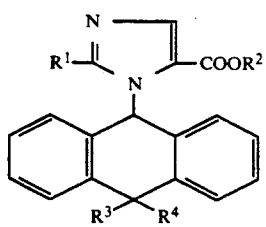

| Comp. No. | R¹ | R² | R³ | R⁴ |
|---|---|---|---|---|
| 16.01 | SH | $CH_3$ | $CH_3$ | $CH_3$ |
| 16.02 | H | $CH_3$ | $CH_3$ | $CH_3$ |
| 16.03 | H | $C_2H_5$ | $CH_3$ | $CH_3$ |
| 16.04 | H | $CH_2-CH_2-OCH_3$ | $CH_3$ | $CH_3$ |
| 16.05 | H | $C_5H_9$-c | $CH_3$ | $CH_3$ |
| 16.06 | H | $C_4H_9$-n | $CH_3$ | $CH_3$ |
| 16.07 | SH | $CH_3$ | $C_2H_5$ | $C_2H_5$ |
| 16.08 | H | $CH_3$ | $C_2H_5$ | $C_2H_5$ |
| 16.09 | SH | $CH_3$ | —$(CH_2)_5$— | |
| 16.10 | H | $CH_3$ | —$(CH_2)_5$— | |

TABLE 17

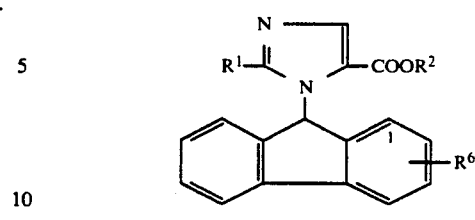

| Comp. No. | R¹ | R² | R⁶ | physical data |
|---|---|---|---|---|
| 17.01 | H | $CH_3$ | H | mp. 146° C. |
| 17.02 | SH | $CH_3$ | H | mp. 208° C. (dec.) |
| 17.03 | H | $CH_3$ | 1-$CH_3$ | |
| 17.04 | SH | $CH_3$ | 1-$CH_3$ | |
| 17.05 | H | $C_2H_5$ | H | |
| 17.06 | H | $C_2H_5$ | 1-$CH_3$ | |
| 17.07 | H | H | H | mp. 237.2° C. |
| 17.08 | SH | H | H | |
| 17.09 | H | H | 1-$CH_3$ | |
| 17.10 | SH | H | 1-$CH_3$ | |

TABLE 18

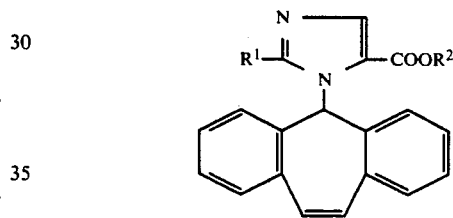

| Comp. No. | R¹ | R² |
|---|---|---|
| 18.01 | SH | $CH_3$ |
| 18.02 | H | $CH_3$ |
| 18.03 | H | $C_2H_5$ |
| 18.04 | H | $C_6H_{11}$-c |

TABLE 19

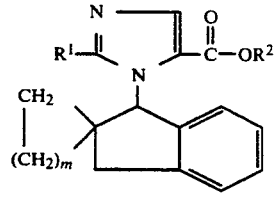

| Comp. No. | R¹ | R² | m | physical data |
|---|---|---|---|---|
| 19.01 | SH | $CH_3$ | 1 | |
| 19.02 | H | $CH_3$ | 1 | |
| 19.03 | SH | $CH_3$ | 2 | |
| 19.04 | H | $CH_3$ | 2 | |
| 19.05 | SH | $CH_3$ | 3 | mp. 160–161.5° C. |
| 19.06 | H | $CH_3$ | 3 | resin |
| 19.07 | SH | $CH_3$ | 4 | mp. 210–212° C. |
| 19.08 | H | $CH_3$ | 4 | mp. 133–135° C. |

TABLE 20

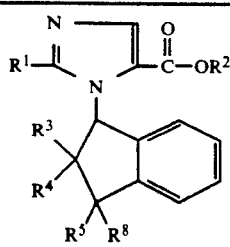

| Comp. No. | R¹ | R² | R³ | R⁴ | R⁵ | R⁸ | physical data |
|---|---|---|---|---|---|---|---|
| 20.01 | SH | $CH_3$ | $CH_3$ | $CH_3$ | $CH_3$ | H | cis/solid |
| 20.02 | H | $CH_3$ | $CH_3$ | $CH_3$ | $CH_3$ | H | cis/$HNO_3$/mp. 133.1° C. |
| 20.03 | SH | $CH_3$ | $CH_3$ | $CH_3$ | $CH_3$ | $CH_3$ | solid |
| 20.04 | H | $CH_3$ | $CH_3$ | $CH_3$ | $CH_3$ | $CH_3$ | $HNO_3$/mp. 155.6° C. |
| 20.05 | SH | $CH_3$ | $CH_3$ | H | $CH_3$ | $CH_3$ | |
| 20.06 | H | $CH_3$ | H | $CH_3$ | $CH_3$ | $CH_3$ | |
| 20.07 | H | $CH_3$ | $CH_3$ | $CH_3$ | $NHCOCH_3$ | H | mp. 70° C. (dec.) |
| 20.08 | H | $CH_3$ | $CH_3$ | $CH_3$ | $OCH_3$ | H | oil |
| 20.09 | H | $CH_3$ | $CH_3$ | $CH_3$ | Br | Br | mp. 138° C. (dec.) |
| 20.10 | H | $CH_3$ | $CH_3$ | $CH_3$ | $OCH_3$ | $OCH_3$ | mp. 140–141° C. |
| 20.11 | H | $CH_3$ | $CH_3$ | $CH_3$ | $OC_2H_5$ | $OC_2H_5$ | mp. 112–115° C. |
| 20.12 | H | $CH_3$ | $CH_3$ | $CH_3$ | F | F | mp. 96–97° C. |

TABLE 21

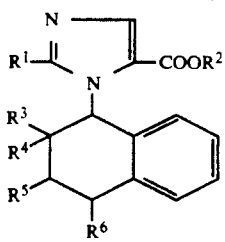

| Comp. No. | R¹ | R² | R³ | R⁴ | R⁵ | R⁶ | physical data |
|---|---|---|---|---|---|---|---|
| 21.01 | H | $CH_3$ | $CH_3$ | $CH_3$ | Br | Br | (1α,3β,4α)/mp. 130–132° C. |
| 21.02 | H | $CH_3$ | $CH_3$ | $CH_3$ | Br | $OCH_3$ | (1α,3β,4α)/mp. 103–105° C. |
| 21.03 | H | $CH_3$ | $CH_3$ | $CH_3$ | Br | $OC_2H_5$ | (1α,3β,4α)/resin |
| 21.04 | H | $CH_3$ | $CH_3$ | $CH_3$ | H | Cl | cis/mp. 146–147° C. |
| 21.05 | H | $CH_3$ | $CH_3$ | $CH_3$ | H | Cl | trans/mp. 94–96° C. |
| 21.06 | H | $CH_3$ | $CH_3$ | $CH_3$ | Cl | $OCH_3$ | |
| 21.07 | H | $CH_3$ | $CH_3$ | $CH_3$ | Cl | $OC_2H_5$ | |

The following examples are intended to illustrate the present invention in all its aspects and not to limit it thereto.

A. COMPOSITION EXAMPLES

EXAMPLE 1.

Formulation Examples for solid compounds of formula (I) (percentages are by weight)

| a) Wettable powders | a) | b) | c) |
|---|---|---|---|
| compound No. 1.02 | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethlene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| b) Emulsifiable concentrate | a) | b) |
|---|---|---|
| compound No. 1.03 | 10% | 1% |
| octyphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| c) Dusts | a) | b) |
|---|---|---|
| compound No. 1.03 | 0.1% | 1% |
| talcum | 99.9% | — |
| kaolin | — | 99% |

Usable dusts were obtained by mixing the active ingredient with the carriers, and grinding the mixture in a suitable mill.

| d) Extruder granulate | a) | b) |
|---|---|---|
| compound No. 1.03 | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| e) Coated granulate | |
|---|---|
| compound No. 1.03 | 3% |
| polyethylene glycol (mol. wt. 200) | 2% |

-continued

| e) Coated granulate | |
|---|---|
| kaolin | 95% |

The finely ground active ingredient was uniformly applied, in a mixer, to the kaolin moistened with polyethylene glycol. Non-dusty coated granulates were obtained in this manner.

| f) Suspension concentrate | a) | b) |
|---|---|---|
| compound No. 1.02 | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| g) Salt solution | |
|---|---|
| compound No. 1.02 | 5% |
| isopropylamine | 1% |
| octylphenol polyethylene glycol ether (78 moles of ethylene oxide) | 3% |
| water | 91% |

EXAMPLE 2

Formulation examples for liquid active ingredients of formula (I) (throughout, percentages are by weight)

| a) Emulsifiable concentrates | a) | b) | c) |
|---|---|---|---|
| compound No. 1.60 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| b) Solutions | a) | b) | c) | d) |
|---|---|---|---|---|
| compound No. 1.60 | 80% | 10% | 5% | 95% |
| ethylene glycol monoethyl ether | 20% | — | — | — |
| polyethylene glycol (MG 400) | — | 70% | — | — |
| N-methyl-2-pyrrolidone | — | 20% | — | — |
| epoxidised coconut oil | — | — | 1% | 5% |
| petroleum distillate (boiling range 160-190° C.) | — | — | 94% | — |

These solutions were suitable for application in the form of microdrops.

| c) Granulates | a) | b) |
|---|---|---|
| compound No. 1.60 | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| d) Dusts | a) | b) |
|---|---|---|
| compound No. 1.60 | 2% | 5% |
| highly dispersed silicic acid | 1% | 5% |
| talcum | 97% | — |
| kaolin | — | 90% |

B. BIOLOGICAL EXAMPLES

EXAMPLE 3

Preemergence herbicidal action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which on account of their insufficient solubility could not be formulated to emulsifiable concentrates. Two different concentration series were used, corresponding to 1 and 0.5 kg of test compound per hectare respectively.

The seed dishes were kept in the greenhouse at 22°~25° C. and 50~70% relative humidity. The test was evaluated 3 weeks later in accordance with the following rating:

1 = plants had not germinated or were totally withered
2-3 = very strong action
4-6 = average action
7-8 = slight action
9 = no action In this test, the tested compounds of formula (I) were most effective against monocot grass weeds, whereas no or only insignificant damage was caused to cultivated plants such as maize at the given rates of application.

| Results: Preemergence test | | | | | | | | |
|---|---|---|---|---|---|---|---|---|
| dosage kg a.i./ha plant tested | Comp. 1 | 1.01 0.5 | Comp. 1 | 1.02 0.5 | Comp. 1 | 1.03 0.5 | Comp. 1 | 1.08 0.5 |
| maize | 9 | 9 | 8 | 9 | 8 | 9 | 9 | 9 |
| alopecurus myos. | 2 | 2 | 2 | 2 | 2 | 2 | 2 | 2 |
| digitaria sang. | — | — | 1 | 1 | 1 | 1 | 1 | 1 |
| echinochloa c.g. | 1 | 1 | 1 | 3 | 1 | 1 | 1 | 1 |
| soybeans | | | | | | | | |
| cotton | | | | | | | | |
| sunflower | | | | | | | | |

-continued

Results: Preemergence test

| | | | | | | | | |
|---|---|---|---|---|---|---|---|---|
| sida spinosa | — | — | 4 | 4 | 1 | 1 | 2 | 3 |
| amaranthus ret. | — | — | 4 | 4 | 1 | 1 | 2 | 2 |
| chenopodium sp. | 3 | 3 | 3 | 3 | 1 | 1 | 1 | 1 |
| solanum nigrum | — | — | 3 | 3 | 1 | 1 | 1 | 1 |
| chrysanthe. leuc. | — | — | 2 | 2 | 2 | 2 | 2 | 2 |
| galium aparine | 3 | 4 | 2 | 2 | 1 | 1 | 2 | 3 |
| viola tricolor | 3 | 3 | 2 | 3 | 1 | 1 | 1 | 1 |
| veronica sp. | — | — | 2 | 2 | 1 | 1 | 1 | 1 |

| dosage kg a.i/ha plant tested | Comp. 1 | 1.16 0.5 | Comp. 1 | 1.17 0.5 | Comp. 1 | 4.01 0.5 | Compound 1 | 6.03 0.5 |
|---|---|---|---|---|---|---|---|---|
| maize | 9 | 9 | 9 | 9 | 8 | 9 | 9 | 9 |
| alopecurus myos. | 5 | 6 | 2 | 2 | 3 | 4 | 6 | 6 |
| digitaria sang. | 1 | 1 | 1 | 1 | 1 | 1 | 1 | 1 |
| echinochloa c.g. | 2 | 2 | 1 | 1 | 1 | 1 | 1 | 1 |
| soybeans | | | | | | | 9 | 9 |
| cotton | | | | | | | 9 | 9 |
| sunflower | | | | | | | 9 | 9 |
| sida spinosa | 3 | 3 | 1 | 2 | 2 | 3 | 3 | 3 |
| amaranthus ret. | 3 | 3 | 2 | 2 | 2 | 3 | 2 | 3 |
| chenopodium sp. | 3 | 4 | 1 | 1 | 1 | 1 | 3 | 3 |
| solanum nigrum | 2 | 2 | 1 | 1 | 2 | 2 | 2 | 2 |
| chrysanthe. leuc. | 3 | 3 | 2 | 2 | 4 | 6 | 2 | 6 |
| galium aparine | 4 | 5 | 2 | 3 | 2 | 3 | 2 | 3 |
| viola tricolor | 3 | 4 | 1 | 1 | 2 | 2 | 3 | 3 |
| veronica sp. | 2 | 2 | 1 | 1 | 1 | 1 | 1 | 1 |

—: not tested

EXAMPLE 4

Postemergence herbicidal action (Contact herbicide):

A large number of weeds and cultivated plants were sprayed postemergence in the 4- to 6-leaf stage with an aqueous active ingredient dispersion in rates of 4 and 2 kg of test compound per hectare and kept at 24°–26° C. and 45–60% relative humidity. The test was evaluated at least 15 days after treatment in accordance with the same rating as employed in the preemergence test.

In this test, the compounds of formula (I) were also most effective against the tested weeds. The cultivated plants such as maize and rice were either not damaged or only damaged at higher application rates of the tested compounds.

Results: Postemergence test

| dosage g a.i/ha plant tested | Comp. 4 | 1.06 2 | Comp. 4 | 4.01 2 |
|---|---|---|---|---|
| maize | 8 | 9 | 3 | 4 |
| rice, dry | 9 | 9 | 8 | 9 |
| xanthium sp. | 3 | 4 | 2 | 2 |
| chenopodium sp. | 4 | 5 | 2 | 2 |
| ipomoea | 4 | 5 | 3 | 3 |
| sinapis | 4 | 7 | 4 | 4 |
| galium aparine | 5 | 5 | 3 | 3 |

-continued

Results: Postemergence test

| dosage g a.i/ha plant tested | Comp. 4 | 1.06 2 | Comp. 4 | 4.01 2 |
|---|---|---|---|---|
| viola tricolor | 4 | 6 | 2 | 3 |

EXAMPLE 5

Herbicidal action in transplanted rice crops 25 days old rice shoots of the variety "Yamabiko" were transplanted into large plastic containers. Into the same containers seeds of the weeds occuring in rice crops, namely alisma, ammania, cyperus, echinochloa, eleocharis, fimbristylis, scirpus and monochoria, were sown between the rice plants. The containers were watered to such an extent, that a water layer of 2.5 cm covered the surface. After 3 days under greenhouse conditions, the diluted aqueous dispersions of the active compounds were added to the water layer at a rate of application of 500, 250, 125, 60, 30 and 15 g a.i. per hectare. The containers were then kept covered with water at a temperature 25° C. and high humidity in a greenhouse for 4 weeks. The evaluation of the tests was made in accordance with the rating given in Example 3.

| | Compound No. | | | | | | | | | | | | | | | | | | | |
|---|---|---|---|---|---|---|---|---|---|---|---|---|---|---|---|---|---|---|---|---|
| | 1.01 in g a.i. per hectare | | | | | | 1.02 in g a.i. per hectare | | | | | | 1.03 in g a.i. per hectare | | | | | | 1.04 in g a.i. per hectare | | |
| Tested plant | 500 | 250 | 125 | 60 | 30 | 15 | 500 | 250 | 125 | 60 | 30 | 15 | 500 | 250 | 125 | 60 | 30 | 15 | 500 | 250 | 125 |
| rice "Yamabiko" | 8 | 9 | 9 | 9 | 9 | 9 | 8 | 9 | 9 | 9 | 9 | 9 | 9 | 9 | 9 | 9 | 9 | 9 | 8 | 9 | 9 |
| alisma | 1 | 1 | 1 | 1 | 2 | 3 | 1 | 2 | 2 | 3 | 3 | 3 | 1 | 1 | 3 | 3 | 3 | 6 | 1 | 1 | 2 |
| ammania | 1 | 2 | 2 | 2 | 2 | 2 | — | — | — | — | — | — | | | | | | | | | |
| cyperus difformia | 1 | 1 | 1 | 1 | 1 | 1 | 1 | 1 | 1 | 1 | 1 | 1 | 1 | 1 | 1 | 1 | 2 | 2 | 1 | 1 | 1 |
| echinochloa c.g. | 1 | 1 | 1 | 1 | 6 | 8 | 1 | 1 | 1 | 1 | 3 | 6 | 1 | 1 | 3 | 6 | 9 | 9 | 2 | 5 | 8 |
| eleocharis | — | — | — | — | — | — | 1 | 1 | 1 | 1 | 1 | 1 | 1 | 1 | 3 | 5 | 5 | 5 | 3 | 5 | 6 |
| fimbristylis | 1 | 1 | 1 | 1 | 1 | 1 | 1 | 1 | 1 | 1 | 1 | 1 | 1 | 1 | 1 | 1 | 1 | 1 | 1 | 1 | 1 |
| scirpus | 1 | 1 | 1 | 1 | 2 | 4 | 1 | 1 | 1 | 3 | 4 | 4 | 1 | 1 | 3 | 5 | 7 | 9 | 1 | 7 | 7 |
| monochoria | 1 | 1 | 1 | 1 | 1 | 3 | 1 | 1 | 1 | 1 | 1 | 1 | 1 | 1 | 1 | 1 | 3 | 9 | 1 | 1 | 3 |

Compound No.

-continued

| Tested plant | 1.04 in g a.i. per hectare | | | 1.11 in g a.i. per hectare | | | | | | 1.12 in g a.i. per hectare | | | | | | 1.16 in g a.i. per hectare | | | |
|---|---|---|---|---|---|---|---|---|---|---|---|---|---|---|---|---|---|---|---|
| | 60 | 30 | 15 | 500 | 250 | 125 | 60 | 30 | 15 | 500 | 250 | 125 | 60 | 30 | 15 | 500 | 250 | 125 | 60 |
| rice "Yamabiko" | 9 | 9 | 9 | 8 | 9 | 9 | 9 | 9 | 9 | 9 | 9 | 9 | 9 | 9 | 9 | 8 | 9 | 9 | 9 |
| alisma | 3 | 5 | 7 | 1 | 1 | 3 | 3 | 3 | 6 | 1 | 1 | 1 | 2 | 6 | 7 | | | | |
| ammania | | | | — | — | — | — | — | — | 1 | 2 | 2 | 2 | 2 | 3 | | | | |
| cyperus difformia | 1 | 3 | 3 | 1 | 1 | 1 | 1 | 1 | 1 | 1 | 1 | 1 | 1 | 1 | 1 | | | | |
| echinochloa c.g. | 8 | 9 | 9 | 1 | 2 | 6 | 8 | 9 | 9 | 1 | 3 | 4 | 8 | 9 | 9 | 1 | 1 | 2 | 3 |
| eleocharis | 7 | 8 | 8 | 1 | 1 | 1 | 1 | 1 | 1 | — | — | — | — | — | — | | | | |
| fimbristylis | 1 | 1 | 1 | 1 | 1 | 1 | 1 | 1 | 1 | 1 | 1 | 1 | 1 | 1 | 2 | | | | |
| scirpus | 7 | 9 | 9 | 1 | 1 | 5 | 6 | 7 | 8 | 1 | 1 | 3 | 7 | 9 | 9 | 1 | 1 | 1 | 2 |
| monochoria | 5 | 5 | 6 | 1 | 1 | 1 | 2 | 4 | 6 | 1 | 1 | 2 | 2 | 4 | 7 | 2 | 3 | 3 | 3 |

| | | Compound No. | | | | | | | | | | | | |
|---|---|---|---|---|---|---|---|---|---|---|---|---|---|---|
| | | 2.01 in g a.i. per hectare | | | | 3.01 in g a.i. per hectare | | | 4.01 in g a.i. per hectare | | | 4.03 in g a.i. per hectare | | | |
| | Tested plant | 500 | 250 | 125 | 60 | 500 | 250 | 125 | 250 | 125 | 60 | 250 | 125 | 60 | 30 |
| | rice "Yamabiko" | 9 | 9 | 9 | 9 | 9 | 9 | 9 | 9 | 9 | 9 | 7 | 8 | 9 | 9 |
| | alisma | | | | | | | | | | | | | | |
| | ammania | | | | | | | | | | | | | | |
| | cyperus difformia | | | | | | | | | | | | | | |
| | echinochloa c.g. | 1 | 2 | 5 | 6 | 3 | 4 | 5 | 1 | 1 | 1 | 1 | 1 | 1 | 1 |
| | eleocharis | | | | | | | | | | | | | | |
| | fimbristylis | | | | | | | | | | | | | | |
| | scirpus | 1 | 1 | 3 | 4 | 1 | 2 | 3 | 1 | 2 | 3 | 1 | 1 | 1 | 1 |
| | monochoria | 1 | 2 | 4 | 5 | 2 | 2 | 4 | 2 | 2 | 3 | 1 | 1 | 1 | 1 |

Results: (—: not tested)

EXAMPLE 6

Herbicidal action against paddy rice associated weeds

The seeds of the waterweeds Echinochloa crus galli and Monochoria vaginalis were sown together in plastic containers (60 cm² surface, 500 ml by volume). The containers were watered up to the soil surface and after three days the water level was raised slightly above the soil surface (3-5 mm). Three days after sowing an aqueous emulsion of the active compound was applied by spraying the containers at a rate of application of 4 kg of a.i. per hectare (dilution 550 l/ha). The containers were kept in a greenhouse for three weeks under conditions optimal for the waterweeds, i.e. at a temperature between 20° and 25° C. and under high humidity.

The evaluation of the tests was made in accordance with the rating given in Example 3.

| compound tested | plant tested | |
|---|---|---|
| | Echinochloa | Monochoria |
| 1.02 | 1 | 1 |
| 1.03 | 1 | 1 |
| 1.04 | 1 | 1 |
| 1.06 | 1 | 1 |
| 1.07 | 3 | 1 |
| 1.08 | 1 | 1 |
| 1.10 | 1 | 1 |
| 1.11 | 1 | 1 |
| 1.12 | 1 | 1 |
| 1.14 | 2 | 1 |
| 1.15 | 2 | 1 |
| 1.16 | 1 | 1 |
| 1.17 | 1 | 1 |
| 1.18 | 1 | 1 |
| 1.41 | 4 | 1 |
| 1.44 | 1 | 1 |
| 1.46 | 2 | 1 |
| 1.47 | 1 | 1 |
| 1.48 | 1 | 1 |
| 1.49 | 1 | 1 |
| 1.60 | 1 | 1 |
| 1.61 | 1 | 1 |
| 1.62 | 1 | 1 |
| 1.64 | 1 | 1 |
| 1.65 | 1 | 1 |
| 1.66 | 1 | 1 |

-continued

| compound tested | plant tested | |
|---|---|---|
| | Echinochloa | Monochoria |
| 1.69 | 1 | 1 |
| 1.70 | 2 | 1 |
| 1.71 | 1 | 1 |
| 1.72 | 1 | 1 |
| 1.73 | 1 | 1 |
| 1.74 | 1 | 1 — |
| 1.75 | 1 | 1 |
| 1.76 | 1 | 1 |
| 1.80 | 3 | 1 |
| 1.81 | 1 | 1 |
| 1.82 | 1 | 1 |
| 1.83 | 1 | 1 |
| 1.84 | 1 | 1 |
| 1.85 | 1 | 1 |
| 1.88 | 1 | 1 |
| 1.91 | 1 | 1 |
| 1.92 | 4 | 1 |
| 1.93 | 1 | 1 |
| 1.94 | 1 | 1 |
| 1.95 | 1 | 1 |
| 1.97 | 1 | 1 |
| 1.101 | 1 | 1 |
| 1.102 | 1 | 1 |
| 1.103 | 1 | 1 |
| 1.104 | 1 | 1 |
| 1.105 | 1 | 1 |
| 1.106 | 1 | 1 |
| 1.107 | 1 | 1 |
| 1.108 | 3 | 1 |
| 1.126 | 1 | 1 |
| 1.127 | 1 | 1 |
| 1.140 | 1 | 1 |
| 1.141 | 1 | 1 |
| 1.159 | 1 | 1 |
| 1.165 | 1 | 1 |
| 1.168 | 1 | 1 |
| 1.179 | 1 | 1 |
| 2.19 | 1 | 1 |
| 2.20 | 1 | 1 |
| 2.24 | 1 | 1 |
| 2.25 | 1 | 1 |
| 2.26 | 1 | 1 |
| 2.27 | 1 | 1 |
| 2.28 | 2 | 1 |
| 2.30 | 1 | 1 |
| 2.34 | 1 | 1 |
| 2.35 | 1 | 1 |

-continued

| compound tested | plant tested | |
|---|---|---|
| | Echinochloa | Monochoria |
| 2.37 | 1 | 1 |
| 3.01 | 3 | 1 |
| 3.02 | 1 | 1 |
| 4.01 | 1 | 1 |
| 4.02 | 2 | 1 |
| 4.03 | 1 | 1 |
| 4.04 | 1 | 1 |
| 4.06 | 1 | 1 |
| 4.08 | 1 | 1 |
| 4.20 | 2 | 1 |
| 4.21 | 1 | 1 |
| 4.24 | 4 | 1 |
| 4.32 | 1 | 1 |
| 4.34 | 1 | 1 |
| 4.35 | 1 | 1 |
| 4.36 | 1 | 1 |
| 4.37 | 1 | 1 |
| 4.44 | 1 | 1 |
| 4.47 | 1 | 1 |
| 4.64 | 1 | 1 |
| 4.65 | 1 | 1 |
| 4.66 | 1 | 1 |
| 4.73 | 1 | 1 |
| 4.74 | 1 | 1 |
| 4.75 | 1 | 1 |
| 4.76 | 1 | 1 |
| 4.77 | 1 | 1 |
| 4.105 | 1 | 1 |
| 4.106 | 1 | 1 |
| 4.107 | 1 | 1 |
| 4.110 | 1 | 1 |
| 4.111 | 1 | 1 |
| 4.138 | 1 | 1 |
| 4.28 | 1 | 1 |
| 4.46 | 3 | 1 |
| 4.78 | 1 | 1 |
| 4.112 | 1 | 1 |
| 4.128 | 1 | 1 |
| 4.131 | 1 | 1 |
| 4.133 | 1 | 1 |
| 4.134 | 2 | 1 |
| 6.01 | 1 | 1 |
| 6.02 | 1 | 1 |
| 6.05 | 4 | 1 |
| 6.06 | 1 | 1 |
| 8.01 | 2 | 1 |
| 8.02 | 1 | 1 |
| 8.03 | 1 | 1 |
| 9.16 | 1 | 1 |
| 10.01 | 1 | 1 |
| 10.10 | 1 | 1 |
| 11.02 | 1 | 1 |
| 17.01 | 1 | 1 |
| 19.06 | 1 | 1 |
| 19.07 | 1 | 1 |
| 19.08 | 1 | 1 |
| 20.02 | 1 | 1 |
| 20.04 | 1 | 1 |
| 20.07 | 5 | 1 |
| 20.08 | 1 | 1 |
| 20.12 | 1 | 1 |
| 21.04 | 1 | 1 |
| 21.05 | 1 | 1 |

Results: dosage 4 kg active ingredient per hectare

C. PREPARATORY EXAMPLES

EXAMPLE 7

1-(7-Methoxy-1,2,3,4-tetrahydronaphthalen-1-yl)-2-mercapto-5-imidazolecarboxylic acid methyl ester (compound 1.13)

a) N-(7-Methoxy-1,2,3,4-tetrahydronaphthalen-1-yl)glycine methyl ester.

367.0 g of 1-amino-7-methoxy-1,2,3,4-tetrahydronaphthalene are solved in 1500 ml of diethyl ether. To this solution is dropwise added a solution of 158.3 g of bromoacetic acid methyl ester in 450 ml of diethyl ether. The mixture is stirred at room temperature for 70 hours. The precipitate is separated and the solution is concentrated to dryness, yielding N-(7-methoxy-1,2,3,4-tetrahydronaphthalen-1-yl) glycine methyl ester quantitatively.

b) N-Formyl-N-(7-methoxy-1,2,3,4-tetrahydronaphthalen-1-yl)glycine methyl ester.

2.40 g of N-(7-methoxy-1,2,3,4-tetrahydronaphthalen-1-yl)glycine methyl ester are added dropwise with cooling to 5° C. to 5.52 g of formic acid. Additionally 1.79 g of acetic anhydride are added, and the mixture is kept at room temperature for 70 hours. Destillation under vacuum affords 2.7 g (97% of theory) of N-formyl-N-(7-methoxy-1,2,3,4-tetrahydronaphthalen-1--yl)glycine methyl ester as a colourless resin.

c) A solution of 1.85 g of sodium methylate in 38 ml of tetrahydrofuran is prepared by adding suitable amounts of methanol and sodium hydride to the tetrahydrofuran. With optional cooling to room temperature 6.5 g of formic acid methyl ester and 10.0 g of N-formyl-N-(7-methoxy-1,2,3,4-tetrahydronaphthalen-1-yl)glycine methyl ester are added. After 20 hours the mixture is taken up with 30 ml of deionisized water and 50 ml of diethyl ether. The aqueous phase is separated, and 30 ml of methanol and 8.6 ml of 36% hydrochloric acid are added. The solution is heated to 40°-45° C. and treated with a solution of 5.8 g of potassium thiocyanate in 10 ml of deionisized water. After 24 hours the mixture is heated to 80° C. for 5 hours. Upon cooling 7.3 g (64% of theory) of 1-(7-methoxy-1,2,3,4-tetrahydronaphthalen-1-yl)-2-mercapto-5-imidazolecarboxylic acid methyl ester precipitates, having a melting point of 184°-186° C.

EXAMPLE 8

1-(7-Methoxy-1,2,3,4-tetrahydronaphthalen-1-yl)-5-imidazolecarboxylic acid methyl ester (compound 1.05)

0.22 g of sodium nitrite and 2.85 g of nitric acid are solved in 7 ml of deionisized water. Within 1 hour 3.2 g of 1-(7-methoxy-1,2,3,4-tetrahydronaphthalen-1-yl)-2-mercapto-5-imidazolecarboxylic acid methyl ester are added portionwise at a temperature between 25° C. and 30° C. The precipitate is isolated affording 2.72 g of the nitric acid addition salt of 1-(7-methoxy-1,2,3,4-tetrahydronaphthalen-1-yl)-5-imidazolecarboxylic acid methyl ester. This salt is treated with 10 ml of 10% aqueous sodium carbonate solution. Extracting the aqueous phase with chloroform, and evaporating the organic solvent yields 2.72 g of 1-(7-methoxy-1,2,3,4-tetrahyronaphthalen-1-yl)-5-imidazolecarboxylic acid methyl ester as a colourless resin.

EXAMPLE 9

1-(1,2,3,4-Tetrahydronaphthalen-1-yl)-5-imidazolecarboxylic acid methyl ester (compound 1.02)

33.0 g of ammonium carbonate are added at room temperature to a solution of 15.5 g of N,α-bis-formyl-N-(1,2,3,4-tetrahydronaphthalen-1-yl)glycine methyl ester in 300 ml of xylene. The mixture is heated to 70° C. for 1 hour then the temperature is raised to 120° C. for 3 hours. After concentration the 1-(1,2,3,4-tetrahydronaphthalen-1-yl)-5-imidazolecarboxylic acid methyl ester precipitates from the solution, having a melting point of 63° C.

EXAMPLE 10

1-(1,2,3,4-Tetrahydronaphthalen-1-yl)-5-imidazolecarboxylic acid methyl ester (compound 1.02)

A mixture of 16.5 g of N,α-bis-formyl-N-(1,2,3,4-tetrahydronaphthalen-1-yl) glycine methyl ester, 65.0 g of ammonium acetate and 100 ml of acetic acid are refluxed for 8 hours. Then additional 50 g ammonium acetate are added and the refluxing is continued for further 4 hours. The solution is diluted with 300 ml of water and extracted twice, with 100 ml of toluene each time. The organic phases are combined, concentrated and separated at silica gel by chromatography. Concentration of the eluate yields 1-(1,2,3,4-tetrahydronaphthalen-1-yl) -5-imidazolecarboxylic acid methyl ester, having a melting point of 63° C.

EXAMPLE 11

1-(1,2,3,4-Tetrahydronaphthalen-1-yl)-5-imidazolecarboxylic acid methyl ester (compound 1.02)

A mixture of 16.5 g of N,α-bis-formyl-N-(1,2,3,4-tetrahydronaphthalen-1-yl)glycine methyl ester, 50 ml of formamide and 10 ml of hydrochloric acid are heated to 140° C. for 8 hours. After cooling to room temperature the mixture is extracted with a mixture of 100 ml of water and 100 ml of diethyl ether. The ethereal phase is separated and the aqueous phase is extracted twice, with 100 ml of diethyl ether each time. The combined organic phase are dried over sodium sulfate and concentrated to dryness. The residue crystallizes affording pure 1-(1,2,3,4-tetrahdronaphthalen-1-yl)-5-imidazolecarboxylic acid methyl ester with a melting point of 63° C.

EXAMPLE 12

1-(2,2-Dimethyl-1,2,3,4-tetrahydronaphthalen-1-yl)-2-mercapto-5-imidazolecarboxylic acid methyl ester (compound 1.17)

a) N-(2,2-Dimethyl-1,2,3,4-tetrahydronaphthalen-1-yl)glycine methyl ester.

65.2 g of 1-amino-2,2-dimethyl-1,2,3,4-tetrahydronaphthalene are solved in 250 ml of diethyl ether. To this solution is dropwise added a solution of 28.5 g of bromoacetic acid methyl ester in 150 ml of diethyl ether. The mixture is stirred at room temperature for 70 hours. The precipitate is separated and the solution is concentrated to dryness, yielding N-(2,2-dimethyl-1,2,3,4-tetrahydronaphthalen-1-yl) glycine methyl ester quantitatively.

b) N-Formyl-N-(2,2-dimethyl-1,2,3,4-tetrahydronaphthalen-1-yl)glycine methyl ester.

The complete yield of N-(2,2-dimethyl-1,2,3,4-tetrahydronaphthalen-1-yl)glycine methyl ester of the process a) is added dropwise with cooling to 5° C. to 67.8 ml of formic acid. Additionally 24.9 ml of acetic anhydride are added, and the mixture is kept at room temperature for 70 hours. Destillation under vacuum affords 35.2 g of N-formyl-N-(2,2-dimethyl-1,2,3,4-tetrahydronaphthalen-1-yl)glycine methyl ester having a melting point of 74°-75° C.

c) A solution of 24.6 g of sodium methylate in 500 ml of tetrahydrofuran is prepared by adding suitable amounts of methanol and sodium hydride to the tetrahydrofuran. With optional cooling to room temperature 73.7 g of formic acid methyl ester and 35.2 g of N-formyl-N-(2,2-dimethyl-1,2,3,4-tetrahydronaphthalen-1-yl)glycine methyl ester are added. After 20 hours the mixture is taken up with 350 ml of deionisized water and 700 ml of diethyl ether. The aqueous phase is separated, and 350 ml of methanol and 97.7 of 36% hydrochloric acid are added. The solution is heated to 40°-45° C. and treated with a solution of 66.1 g of potassium thiocyanate in 200 ml of deionisized water. After 24 hours at 40° C. the mixture is heated to 80° C. for 5 hours. Upon cooling 35.8 g of 1-(2,2-dimethyl-1,2,3,4-tetrahydronaphthalen-1-yl) -2-mercapto-5-imidazole-carboxylic acid methyl ester precipitates, having a melting point of 171°-172° C.

EXAMPLE 13

1-(2,2-Dimethyl-1,2,3,4-tetrahydronaphthalen-1-yl)-5-imidazolecarboxylic acid methyl ester (compound 1.03)

5.8 g of sodium nitrite and 55 g of nitric acid are solved in 3100 ml of deionisized water. Within 1 hour 92.2 g of 1-(2,2-dimethyl-1,2,3,4-tetrahydrophthalen-1-yl)-2-mercapto-5-imidazolecarboxylic acid methyl ester are added portionwise at a temperature between 25° C. and 30° C. The precipitate is isolated affording 100.0 g of the nitric acid addition salt of 1-(2,2-dimethyl-1,2,3,4-tetrahydronaphthalen-1-yl)-5-imidazolecarboxylic acid methyl ester. This salt is treated with 250 ml of 10% aqueous sodium carbonate solution. Extracting the aqueous phase with chloroform, and evaporating the organic solvent yields 80.4 g of 1-(2,2-dimethyl-1,2,3,4-tetrahydronaphthalen-1-yl)-5-imidazolecarboxylic acid methyl ester having a melting point of 100°-101° C.

EXAMPLE 14

1-(1,2,3,4-Tetrahydronaphthalen-1-yl)-2-mercapto-5-imidazolecarboxylic acid methyl ester (compound 11.01)

a) R-N-(1,2,3,4-Tetrahydronaphthalen-1-yl)-glycine methyl ester.

The optically pure isomer of R-1-amino-1,2,3,4-tetrahydronaphthalene is prepared as described in U.S. Pat. No. 3,953,506.

51.4 g of R-1-amino-1,2,3,4-tetrahydronaphthalene and 37.1 g of sodium carbonate are dispersed in 300 ml of methanol. 53.6 g of bromoacetic acid methyl ester are added dropwise to this dispersion. The mixture is stirred at room temperature for 100 hours. The precipitate is separated and the solution is concentrated to dryness, yielding the R-N-(1,2,3,4-tetrahydronaphthalen-1-yl) glycine methyl ester quantitatively.

b) R-N-Formyl-N-(1,2,3,4-tetrahydronaphthalen-1-yl)glycine methyl ester.

64.9 g of R-N-(1,2,3,4-tetrahydronaphthalen-1-yl)glycine methyl ester are added dropwise with cooling to 5° C. to 134 ml of formic acid. Additionally 48.9 ml of acetic anhydride are added, and the mixture is kept at room temperature for 70 hours. Destillation under vacuum affords 50.6 g of R-N-formyl-N-(1,2,3,4-tetrahydronaphthalen-1-yl)glycine methyl ester having a melting point of 83°-84° C.

c) A solution of 11.2 g of sodium methylate in 250 ml of tetrahydrofuran is prepared by adding suitable amounts of methanol and sodium hydride to the tetrahydrofuran. With optional cooling to room temperature 35.1 g of formic acid methyl ester and the R-N-formyl-N-(1,2,3,4-tetrahydronaphthalen-1-yl)glycine methyl ester obtained from the process b) are added. After 20 hours the mixture is taken up with 130 ml of deionisized water and 250 ml of diethyl ether. The aqueous phase is separated, and 130 ml of methanol and 46.9 ml of 36% hydrochloric acid are added. The solution is heated to 40°–50° C. and treated with a solution of 31.5 g of potassium thiocyanate in 60 ml of deionisized water. The mixture is stirred at room temperature for 24 hours. During this period 24.4 g of R-1-(1,2,3,4-tetrahydronaphthalen-1-yl)-2-mercapto-5-imidazolecarboxylic acid methyl ester precipitate. After recrystallisation from methanol the product has a melting point of 141°–142° C., $[\alpha]_D^{20} = +97.1°$.

EXAMPLE 15

R-1-(1,2,3,4-Tetrahydronaphthalen-1-yl)-5-imidazolecarboxylic acid methyl ester (compound 11.03)

1.4 g of sodium nitrite and 11.7 ml of nitric acid are solved in 75 ml of deionisized water. Within 1 hour 17.9 g of R-1-(1,2,3,4-tetrahydronaphthalen-1-yl)-2-mercapto-5-imidazolecarboxylic acid methyl ester are added portionwise at a temperature between 25° C. and 30° C. The precipitate is isolated affording the nitric acid addition salt of R-1-(1,2,3,4-tetrahydronaphthalen-1-yl)-5-imidazolecarboxylic acid methyl ester. This salt is treated with 10% aqueous sodium carbonate solution. Extracting the aqueous phase with chloroform, and evaporating the organic solvent yields 7.4 g of R-1-(1,2,3,4-tetrahydronaphthalen-1-yl)-5-imidazolecarboxylic acid methyl ester as a colourless resin, which is purified by chromatography through a silica column. The pure resinous product has a specific rotation $[\alpha]_D^{20} = -25.80°$.

EXAMPLE 16

S-1-(1,2,3,4-Tetrahydronaphthalen-1-yl)-2-mercapto-5-imidazolecarboxylic acid methyl ester (compound 11.02)

a) S-N-(1,2,3,4-Tetrahydronaphthalen-1-yl)-glycine methyl ester.

The optically pure isomer of S-1-amino-1,2,3,4-tetrahydronaphthalene is prepared as described as U.S. Pat. No. 3,953,506.

26.0 g of S-1-amino-1,2,3,4-tetrahydronaphthalene and 18.8 g of sodium carbonate are dispersed in 150 ml of methanol. 27.1 g of bromoacetic acid methyl ester are added dropwise to this dispersion. The mixture is stirred at room temperature for 100 hours. The precipitate is separated and the solution is concentrated to dryness, yielding the S-N-(1,2,3,4-tetrahydronaphthalen-1-yl) glycine methyl ester quantitatively.

b) S-N-Formyl-N-(1,2,3,4-tetrahydronaphthalen-1-yl)glycine methyl ester.

35.0 g of S-N-(1,2,3,4-tetrahydronaphthalen-1-yl)glycine methyl ester are added dropwise with cooling to 5° C. to 72.3 ml of formic acid. Additionally 26.4 ml of acetic anhydride are added, and the mixture is kept at room temperature for 70 hours. Destillation under vacuum affords 20.4 g of S-N-formyl-N-(1,2,3,4-tetrahydronaphthalen-1-yl)glycine methyl ester having a melting point of 86°–87° C.

c) A solution of 4.77 g of sodium methylate in 100 ml of tetrahydrofuran is prepared by adding suitable amounts of methanol and sodium hydride to the tetrahydrofuran. With optional cooling to room temperature 14.4 g of formic acid methyl ester and the S-N-formyl-N-(1,2,3,4-tetrahydronaphthalen-1-yl)glycine methyl ester obtained from the process b) are added. After 20 hours the mixture is taken up with 55 ml of deionisized water and 110 ml of diethyl ether. The aqueous phase is separated, and 55 ml of methanol and 19.2 ml of 36% hydrochloric acid are added. The solution is heated to 40°–50° C. and treated with a solution of 12.9 g of potassium thiocyanate in 25 ml of deionisized water. The mixture is stirred at room temperature for 24 hours. During this period 9.5 g of S-1-(1,2,3,4-tetrahydronaphthalen-1-yl)-2-mercapto-5-imidazolecarboxylic acid methyl ester precipitates. After recrystallisation from methanol the product has a melting point of 141°–142° C., $[\alpha]_D^{20} = -87.9°$.

EXAMPLE 17

S-1-(1,2,3,4-Tetrahydronaphthalen-1-yl)-5-imidazolecarboxylic acid methyl ester (compound 11.04)

0.5 g of sodium nitrite and 4.2 ml of nitric acid are solved in 50 ml of deionisized water. Within 1 hour 6.4 g of S-1-(1,2,3,4-tetrahydronaphthalen-1-yl)-2-mercapto-5-imidazolecarboxylic acid methyl ester are added portionwise at a temperature between 25° C. and 30° C. The precipitate is isolated affording the nitric acid addition salt of S-1-(1,2,3,4-tetrahydronaphthalen-1-yl)-5-imidazolecarboxylic acid methyl ester. This salt is treated with 10% aqueous sodium carbonate solution. Extracting the aqueous phase with chloroform, and evaporating the organic solvent yields 2.1 g of S-1-(1,2,3,4-tetrahydronaphthalen-1-yl)-5-imidazolecarboxylic acid methyl ester as a colourless resin, which is purified by chromatography through a silica column. The pure resinous product has a specific rotation of $[\alpha]_D^{20} = +23.6°$.

EXAMPLE 18

1-(2,2-Dimethyl-indan-1-yl)-2-mercapto-5-imidazolecarboxylic acid methyl ester (Compound 4.01)

a) N-(2,2-Dimethyl-indan-1-yl)glycine methyl ester.

702 g of 1-amino-2,2-dimethyl-indan and 462 g of sodium carbonate are dispersed in 2618 ml of methanol. 404 g of bromoacetic acid methyl ester are added dropwise to this dispersion. The mixture is stirred at room temperature for 17 hours. The precipitate is separated and the solution is concentrated to dryness, yielding the glycine methyl ester quantitatively.

b) N-Formyl-N-(2,2-dimethyl-indan-1-yl)glycine methyl ester.

936 g of N-(2,2-dimethyl-indan-1-yl)glycine methyl ester are added dropwise with cooling to 5° C. to 1817 ml of formic acid. Additionally 664 ml of acetic anhydride are added, and the mixture is kept at room temperature for 18.5 hours. Destillation under vacuum affords 1015 g of N-formyl-N-(2,2-dimethyl-indan-1-yl)glycine methyl ester.

c) 1-(2,2-Dimethyl-indan-1-yl)-2-mercapto-5-imidazolecarboxylic acid methyl ester.

A mixture of 57.8 g of sodium methylate in 1000 ml of tetrahydrofuran is prepared by adding suitable amounts of methanol and sodium hydride to the tetrahydrofuran. With optional cooling to room temperature 180 ml of formic acid methyl ester and the 261 g N-formyl-N-(2,2-dimethyl-indan-1-yl)glycine methyl ester obtained from the process b) are added. After 20 hours the mixture is taken up with 810 ml of deionized water and 1.5 l of hexane. The aqueous phase is separated, and 810 ml of methanol and 240 g of 32% hydrochloric acid are added. The solution is heated to 40°–50° C. and treated with a solution of 138 g of potassium thiocyanate in 300 ml of deionized water. The mixture is stirred at room temperature for 48 hours. During this period 312 g of 1-(2,2-dimethyl-indan-1-yl)-2-mercapto-5-imidazolecarboxylic acid methyl ester precipitates. After recrystallisation from methanol the product has a melting point of 172°–173° C.

EXAMPLE 19

1-(2,2-Dimethyl-indan-yl)-5-imidazolecarboxylic acid methyl ester (compound 4.03)

2 g of sodium nitrite and 17.4 ml of nitric acid are solved in 140 ml of deionisized water. Within 20 min. 28 g of 1-(2,2-dimethyl-indan-1-yl)-2-mercapto-5-imidazolecarboxylic acid methyl ester are added portionwise at a temperature between 30° C. and 50° C. The reaction mixture is treated with conc. aqueous sodium hydroxide solution. Extracting the aqueous phase with chloroform, and evaporating the organic solvent yields 24.2 g of 1-(2,2-dimethyl-indan-1-yl)-5-imidazolecarboxylic acid methyl ester as a colourless product (m.p. 96°–97° C.).

EXAMPLE 20

S-1-(2,2-Dimethyl-indan-1-yl)-5-imidazolecarboxylic acid methyl ester and
R-1-(2,2-dimethyl-indan-1-yl)-5-imidazolecarboxylic acid methyl ester (compounds 4.53 and 4.54)

The racemic mixture of 1-amino-2,2-dimethyl-indan is treated with the R- and S-isomers of N-benzoyl-glutamic acid in order to separate the R- and S-isomers of 1-amino-2,2-dimethyl-indan. The procedure is carried out analogous to the method described in U.S. Pat. No. 3,953,506 for the separation of R- and S-tetrahydronaphthylamine.

The thus obtained products are:

(+)-1-amino-2,2-dimethyl-indan, oil, $[\alpha]_D^{20} = +22.1°$; and
(−)-1-amino-2,2-dimethyl-indan, oil, $[\alpha]_D^{20} = -22.7°$.

Following the procedures of examples 18 and 19 and using the above pure isomers as starting materials, the following intermediates and final products are obtained:

(+)-N-(2,2-dimethyl-indan-1-yl)glycine methyl ester, oil, $[\alpha]_D^{20} = +51.3°$;
(−)-N-(2,2-dimethyl-indan-1-yl)glycine methyl ester, oil, $[\alpha]_D^{20} = -53.2°$;
(+)-N-formyl-N-(2,2-dimethyl-indan-1-yl)glycine methyl ester, resin, $[\alpha]_D^{20} = +65.4°$;
(−)-N-formyl-N-(2,2-dimethyl-indan-1-yl)glycine methyl ester, resin, $[\alpha]_D^{20} = -72.6°$;
(−)-1-(2,2-dimethyl-indan-1-yl)-2-mercapto-5-imidazolecarboxylic acid methyl ester, m.p. 115°–118° C., $[\alpha]_D^{20} = -140.5°$; (compound 4.51)
(+)-1-(2,2-dimethyl-indan-1-yl)-2-mercapto-5-imidazolecarboxylic acid methyl ester, m.p. 110°–112° C., $[\alpha]_D^{20} = +144°$; (compound 4.52)
(+)-1-(2,2-dimethyl-indan-1-yl)-5-imidazolecarboxylic acid methyl ester, m.p. 73°–75° C., $[\alpha]_D^{20} = +76.3°$; (compound 4.53); and
(−)-1-(2,2-dimethyl-indan-1-yl)-5-imidazolecarboxylic acid methyl ester, m.p. 73°–75° C., $[\alpha]_D^{20} = -72.9°$; (compound 4.54).

EXAMPLE 21

1,4-cis-1-(2,2-Dimethyl-4-chlorotetraline-1-yl)-5-imidazolecarboxylic acid methyl ester and
1,4-trans-(2,2-dimethyl-4-chlorotetralin-1-yl)-5-imidazolecarboxylic acid methyl ester (compounds 21.04 and 21.05)

a) 1-(2,2-Dimethyl-4-oxo-tetralin-1-yl)-5-imidazolecarboxylic acid methyl ester.

142 g of 1-(2,2-dimethyl-tetralin-1-yl)-5-imidazolecarboxylic acid methyl ester are dispersed in 1 liter of deionisized water. The suspension is heated to +87° C., and within a period of 1.5 hours a total of 335 g of ammoniaperoxodisulfate is added portionwise in such a manner, that the temperature does not exceed +90° C. After cooling the reaction mixture to +15° C., the pH-value is adjusted to pH 4 by addition of 335 g of a sodium hydroxide solution 30%. The mixture is extracted with 500 ml of methylene chloride. The organic phase is separated, dried with sodium sulfate, treated with activated carbon and concentrated. Crystallisation of the residue from diethyl ether yields 42 g of 1-(2,2-dimethyl-4-oxo-tetralin-1-yl)-5-imidazolecarboxylic acid methyl ester, having a melting point of 93°–95° C.

b) 1,4-cis-1-(2,2-Dimethyl-4-hydroxy-tetralin-1-yl)-5-imidazole carboxylic acid methyl ester and 1,4-trans-1-(2,2-dimethyl-4-hydroxy-tetralin-1-yl)-5-imidazolecarboxylic acid methyl ester.

A solution of 20.9 g of 1-(2,2-dimethyl-4-oxo-tetralin-1-yl)-5-imidazolecarboxylic acid methyl ester in 200 ml of methanol is treated with 4 g of sodium borohydride at room temperature for 0.5 hours. The solvent is distilled off and the residue is chromatographically separated over silica gel with a mixture of diethyl ester and methylene chloride (1:1 by volume). 11 Parts of 1,4-trans-1-(2,2-dimethyl-4-hydroxytetraline-1-yl)-5-imidazole carboxylic acid methyl ester; mp. 135°–136° C. and 3 g of 1,4-cis-1-(2,2-dimethyl-4-hydroxy-tetralin-1-yl)-5-imidazolecarboxylic acid methyl ester; mp. 179°–180° C. are obtained.

c) A solution of 20 g of 1,4-trans-1-(2,2-dimethyl-4-hydroxy-tetralin-1-yl)-5-imidazolecarboxylic acid methyl ester in 200 ml of pyridine is treated with 0.3 g of 4-dimethylaminopyridine and 14.0 g of p-toluenesulfonic acid chloride at room temperature for 14 hours. The reaction mixture is concentrated to a residue of 50 ml and separated on a silica gel column with a mixture of diethyl ester and hexane (2:1 by volume). The yellowish slurry of crystals is treated with diethyl ether/hexane (10:1 by volume). The colourless precipitate is filtered off, yielding 1,4-cis-1-(2,2-dimethyl-4-chlorotetralin-1-yl)-5-imidazole carboxylic acid methyl ester, mp. 146°–147° C.

d) A solution of 9.8 g of 1,4-cis-1-(2,2-dimethyl-4-hydroxytetralin-1-yl)-5-imidazolecarboxylic acid methyl ester in 100 ml of pyridine is treated with 0.3 g of 4-dimethylaminopyridine and 7.5 g of p-toluenesulfonic acid chloride at room temperature for 14 hours. The reaction mixture is concentrated to dryness and chromatographed at a silica gel column with a diethyl ether/hexane mixture (2:1 by volume). Crystallization of the concentrated eluent yields 2.1 g of 1,4-trans-1-(2,2-dimethyl-4-chlorotetralin-1-yl)-5-imidazolecarboxylic acid methyl ester, having a melting point of 94°–96° C.

EXAMPLE 22

3,4-trans-1,4-cis-1-(2,2-dimethyl-3-bromo-4-methoxy-tetralin-1-yl)-5-imidazolecarboxylic acid methyl ester (compound 21.02)

a) 1-(1,2-Dihydro-2,2-dimethyl-naphthalin-1-yl)-5-imidazolecarboxylic acid methyl ester (compound 10.01)

5 ml of triethylamine are added dropwise at room temperature to a mixture of 1.8 g of methanesulfonic acid chloride and 5.2 g of 1,4-trans-1-(2,2-dimethyl-4-hydroxy-tetralin-1-yl)-5-imidazolecarboxylic acid methyl ester in 100 ml of ethyl acetate. After a period of 1 hour the precipitate is filtered off and the filtrate is concentrated. The residue is chromatographed at silica gel with a diethyl ether/methylene chloride mixture (1:1 by volume), yielding 2.5 g of 1-(1,2-dihydro-2,2-dimethylnaphthalin-1-yl)-5-imidazolecarboxylic acid methyl ester, m.p. 60°-62° C.

b) A solution of 2.76 g of N-bromoacetamide in 40 ml of methanol is dropwise added to a solution of 5.6 g of 1-(1,2-dihydro-2,2-dimethylnaphthalin-1-yl)-5-imidazolecarboxylic acid methyl ester in 40 g of methanol. After a reaction period of 14 hours at room temperature, the mixture is concentrated. The residue is taken up with 100 ml of diethyl ether and washed with water. The organic phase is dried with magnesium sulfate and concentrated. The residue is crystallized from ligroin affording 3 g of 3,4-trans-1,4-cis-1-(2,2-dimethyl-3-bromo-4-methoxytetralin-1-yl)-5-imidazolecarboxylic acid methyl ester, mp. 103°-105° C.

EXAMPLE 23

1-(2,2-Dimethyl-1,2-dihydro-4-methoxynaphthalin-1-yl)-5-imidazolecarboxylic acid methyl ester (compound 10.10)

Method a)
1.6 g of 1,8-diazabicylo[5.4.0]undec-7-ene are added to a solution of 3.9 g of 3,4-trans-1,4-cis-1-(2,2-dimethyl-3-bromo-4-methoxytetralin-1-yl)-5-imidazolecarboxylic acid methyl ester in 20 ml of acetonitrile and the mixture is heated to +80° C. for 60 hours. After cooling to room temperature and concentrating, the product is chromatographed at silica gel with a diethyl ether/methylene chloride mixture (1:30 by volume), yielding 2.5 g of 1-(2,2-dimethyl-1,2-dihydro-4-methoxynaphthalin-1-yl)-5-imidazolecarboxylic acid methyl ester with a melting point of 103°-104° C.

Method b)
A solution of 2.2 g of potassium tert. butylate in 60 ml of tetrahydrofuran is dropwise added to a solution of 3.0 g of 1-(2,2-dimethyl-4-oxo-tetralin-1-yl)-5-imidazolecarboxylic acid methyl ester in 150 ml of tetrahydrofuran. A solution of 5 g of methyliodide in 20 ml of tetrahydrofuran is added. After total consumption of the starting material the mixture is diluted with 100 ml of diethyl ether and washed with sodium bicarbonate solution and brine. The organic phase is dried with magnesium sulfate, treated with activated carbon, and concentrated. The residue is chromatographed at a silica gel column with a diethyl ether/hexane mixture (2:1), 0.9 g of 1-(2,2-dimethyl-1,2-dihydro-4-methoxynaphthalin-1-yl)-5-imidazolecarboxylic acid methyl ester with a melting point of 102°-104° C. are obtained.

EXAMPLE 24

3,4-trans-1,4-cis-1-(2,2-dimethyl-3,4-dibromotetralin-1-yl)-5-imidazolecarboxylic acid methyl ester (compound 21.01)

An emulsion of 2.1 g of bromine in 20 ml of diethyl ether is added to a solution of 2.8 g of 1-(2,2-dimethyl-1,2-dihydronaphthalin-1-yl)-5-imidazolecarboxylic acid methyl ester in 50 ml of diethyl ether. After a reaction time of 20 minutes the mixture is concentrated to dryness and the residue is chromatographed at a silica gel column with methylene chloride, yielding 3 g of 3,4-trans-1,4-cis-1-(2,2-dimethyl-3,4-dibromotetralin-1-yl)-5-imidazolecarboxylic acid methyl ester; mp. 130°-132° C.

EXAMPLE 25

1-(2,2-dimethyl-4-bromo-1,2-dihydronaphthalin-1-yl)-5-imidazole carboxylic acid methyl ester (compound 10.09)

1.6 g of 1,8-diazabicyclo[5.4.0]undec-7-ene are added to a solution of 4.4 g of 3,4-trans-1,4-cis-1-(2,2-dimethyl-3,4-dibromotetralin-1-yl)-5-imidazolecarboxylic acid methyl ester in 50 ml of acetonitrile. The reaction mixture is heated to +80° C. for 60 hours. After cooling to room temperature, the solvent is distilled off and the residue is purified by chromatography at a silica gel column with a diethyl ether/methylene chloride mixture (1:30 by volume), yielding 2.9 g of 1-(2,2-dimethyl-4-bromo-1,2-dihydronaphthalin-1-yl)-5-imidazolecarboxylic acid methyl ester; mp. 101°-103° C.

EXAMPLE 26

1-(2,2-dimethyl-4-bromo-1,2-dihydronaphthalin-1-yl)-5-imidazole carboxylic acid methyl ester (compound 10.09)

A solution of 8.5 g of 1-(2,2-dimethyltetralin-1-yl)-5-imidazolecarboxylic acid methyl ester in 100 ml of carbon tetrachloride is treated with 8.6 g of 1,3-dibromo-5,5-dimethylhydantoin and heated to reflux for 1 hour, while the reaction vessel is exposed to a 100W-irradiation lamp. The mixture is cooled to room temperature and concentrated to dryness. Chromatography of the residue at a silica gel column with methylene chloride affords 5.6 g of 1-(2,2-dimethyl-4-bromo-1,2-dihydronaphthalin-1-yl)-5-imidazolecarboxylic acid methyl ester in form of colourless crystals; mp. 101°-103° C.

EXAMPLE 27

1-(2,2-Dimethyl-3,3-difluoro-indan-1-yl)-5-imidazolecarboxylic acid methyl ester (compound 20.12)

a) 1-(2,2-Dimethyl-3-oxo-indan-1-yl)-5-imidazolecarboxylic acid methyl ester.

A mixture of 30 g of 1-(2,2-dimethyl-indan-1-yl)-5-imidazolecarboxylic acid methyl ester, 150 ml of water and 17 g of sulfuric acid is heated to +80° C. Within a period of 1.5 hours an aqueous solution of 114 g of ammoniaperoxodisulfate is added dropwise. The reaction mixture is cooled to +7° C. and the pH-value is adjusted to pH 3 by addition of a 30% sodium hydroxide solution. The mixture is twice extracted with 200 ml of methylene chloride. The combined organic extracts are dried with sodium sulfate and concentrated to dryness. The residue is taken up with a small amount of methylene chloride and diluted with diethyl ether. The resulting suspension is filtered and the filtrate is concentrated and crystallized from a diethyl ether/hexane mixture affording 19 g of 1-(2,2-dimethyl-3-oxo-indan-1-yl)-5-imidazolecarboxylic acid methyl ester, mp. 104°-108° C.

b) A mixture of 11.4 g of 1-(2,2-dimethyl-3-oxo-indan-1-yl)-5-imidazolecarboxylic acid methyl ester, 43 g of sulfur tetrafluoride and 160 g of hydrogen fluoride is heated for 24 hours to +50° C. in an acid-resistant autoclave. The pressure is about 7 bars. The unreacted hydrogen fluoride is removed and the residue is taken up with methylene chloride. The organic phase is neutralized with sodium bicarbonate, washed with water, dried with sodium sulfate and concentrated to dryness. Chromatography of the residue at a silica gel column with a diethyl ether/hexane mixture (3:1 by volume) affords 8.4 g of 1-(2,2-dimethyl-3,3-difluoro-indan-1-yl)-5-imidazolecarboxylic acid methyl ester, mp. 96°-97° C.

EXAMPLE 28

1-(2,2-dimethyl-4-chloro-indan-1-yl)-5-imidazolecarboxylic acid methyl ester (compound 4.104)

a) 1-Amino-4-chloro-2,2-dimethylindane.

22.4 g of pulverized potassium hydroxide and 0.1 g of 18-dibenzocrown-6 are added portionwise to a solution of 25 g of 4-chloroindanone and 56.7 g of methyl iodide in 120 ml of dimethylformamide in such a manner that the temperature is kept below +70° C. When the exothermic reaction is over, 5.6 g of methyl iodide are added and the mixture is agitated for another 0.5 hours. 200 ml of cold water are added and the mixture is extracted with diethyl ether. The organic phase is dried, with sodium sulfate and concentrated to dryness, affording 27.4 g of crude 2,2-dimethyl-4-chloro-indanone. This crude product is directly subjected to the Leuckart-Wallach amine preparation as described in "Organic Reactions vol. 5, page 301ff, John Wiley & Sons, New York 1949", yielding pure 1-amino-4-chloro-2,2-dimethyl-indane.

b) N-Cyano-N'-(2,2-dimethyl-4-chloroindan-1-yl)-formamidine.

18.6 g of 1-amino-4-chloro-2,2-dimethylindane and 9.8 g of ethyl-N-cyano-imidoformiate are refluxed for 2.5 hours in 50 ml of ethanol. The solvent is distilled off and the residue is taken up in diethyl ether. The precipitate is collected, yielding 21 g of N-cyano-N'-(2,2-dimethyl-4-chloroindan-1-yl)formamidine; mp. 173°-175° C.

c) 12.7 g of potassium carbonate are added to a solution of 21 g of N-cyano-N'-(2,2-dimethyl-4-chloroindan-1-yl)formamidine in 80 ml of dimethylformamide. 14.1 g of methyl bromoacetate are added dropwise. After the exothermic reaction has ceased the mixture is agitated for 1.5 hours at +50° C. another portion of 12.7 g of potassium carbonate is added and the mixture is stirred for 18 hours at +100° C. The precipitate is filtered off from the hot solution and washed with 30 g of hot dimethylformamide. The combined filtrates are dropwise added at +60° C. to a solution of 14.2 g of tert. butylnitrite in 30 ml of dimethylformamide. Immediate evolution of nitrogen is observed and the temperature of the mixture rises to +67° C. After 30 minutes the dropwise addition is completed. The mixture is maintained at +70° to +75° C. for 2.5 hours and then poured into ice-water and extracted with ethyl acetate. The organic phase is washed with brine, dried with sodium sulfate and concentrated to dryness. The residue is purified by chromatography at a silica gel column with an ethyl acetate/hexane mixture (1:2 by volume), affording 12.7 g of 1-(2,2-dimethyl-4-chloro-indan-1-yl)-5-imidazolecarboxylic acid methyl ester, having a melting point of 111°-113° C.

EXAMPLE 29

1-(2,2-Dimethyl-3,3-dibromo-indan-1-yl)-5-imidazolecarboxylic acid methyl ester (compound 20.09)

10.8 g of 1-(2,2-dimethyl-indan-1-yl)-5-imidazolecarboxylic acid methyl ester and 11.4 g of 1,3-dibromo-5,5-dimethyl hydantion are suspended in 100 ml of carbon tetrachloride and heated to +78° C. The reaction mixture is irradiated for 1 hour with a 100W-irradiation lamp. The mixture is cooled to +20° C., filtrated and concentrated to dryness. The residue is taken up with 50 ml of diethyl ethyl and filtered. The filtrate is treated with a small amount of hexane in order to complete the formation of a precipitate, yielding 6.8 g of 1-(2,2-dimethyl-3,3-dibromo-indan-1-yl)-5-imidazolecarboxylic acid methyl ester in the form of colourless crystals; mp. 138° C.

EXAMPLE 30

1-(2,2-dimethyl-3,3-dimethoxy-indan-1-yl)-5-imidazolecarboxylic acid methyl ester (compound 20.10).

2.5 g of 1-(2,2-dimethyl-3,3-dibromo-indan-1-yl)-5-imidazolecarboxylic acid methyl ester are solved in 20 ml of methanol. The solution is kept at +25° C. for 0.5 hours, then 1.5 g of triethylamine are added. The mixture is concentrated to dryness and taken up with 50 ml of diethyl ether. The precipitate is filtered off, and the filtrate is concentrated. Crystallization of the residue from hexane affords 1.3 g of 1-(2,2-dimethyl-3,3-dimethoxy-indan-1-yl)-5-imidazolecarboxylic acid methyl ester as colourless crystalls; mp. 140°-141° C.

EXAMPLE 31

1-(2,2-dimethyl-3-acetamino-indan-1-yl)-5-imidazolecarboxylic acid methyl ester (compound 20.07)

a) 1,3-cis-1-(2,2-dimethyl-3-hydroxy-indan-1-yl)-5-imidazolecarboxylic acid methyl ester.

A solution of 5.7 g of 1-(2,2-dimethyl-3-oxo-indan-1-yl)-5-imidazolecarboxylic acid methyl ester in 20 ml of methanol is treated with 0.7 g of sodium borohydride. After the vigorous evolution of hydrogen has ceased, the reaction mixture is poured into 100 ml of a 2% hydrochloric acid. The mixture is neutralized with saturated sodium bicarbonate and extracted twice with 100 ml of a diethyl ether/methylene chloride mixture (4:1 by volume). The organic phase is separated, dried with magnesium sulfate and concentrated. The residue is treated with diethyl ether and the precipitate is collected, yielding 2.8 g of 1,3-cis-1-(2,2-dimethyl-3-hydroxy-indan-1-yl)-5-imidazolecarboxylic acid methyl ester, mp. 194°-195° c. The mother-liquor is concentrated, affording 2.5 g of a foamy product, consisting of a 4:1-mixture of the 1,3-trans- and 1,3-cis-isomers of the title product.

b) 6 g of 96% sulfuric acid are added to a solution of 5.7 g of 1,3-cis-1-(2,2-dimethyl-3-hydroxy-indan-1-yl)-5-imidazolecarboxylic acid methyl ester in 100 ml of acetonitrile with vigorous stirring. After 0.5 hours the mixture is concentrated, and taken up with 200 ml of diethyl ether and 200 ml of water. The mixture is neutralized by addition of saturated sodium bicarbonate solution. The organic phase is separated, dried with sodium sulfate and concentrated to dryness, yielding 6.3 g of a 1:1-mixture of 1,3-cis- and 1,3-trans-isomers of 1-(2,2-dimethyl-3-acetamino-indan-1-yl)-5-imidazolecarboxylic acid methyl ester, mp. 70° C.

EXAMPLE 32

1-(2,2-Dimethyl-3-methoxy-indan-1-yl)-5-imidazolecarboxylic acid methyl ester (compound 20.08)

40 g of 96% sulfuric acid are dropwise added to a solution of 2.86 g of 1,3-cis-1-(2,2-dimethyl-3-hydroxyindan-1-yl)-5-imidazolecarboxylic acid methyl ester in 50 ml of absolute methanol. An exothermic reaction is observed, which heats the reaction mixture to +85° C. After 0.5 hours the mixture is cooled to 20° C. and then poured into 200 g of ice-water. The pH-value is adjusted to pH 6.5 by addition of a 30% sodium hydroxide solution. The aqueous mixture is extracted with 200 ml of diethyl ether. The ethereal phase is dried with sodium sulfate and concentrated to dryness. The colourless oily residue consists of 3 g of 1-(2,2-dimethyl-3-methoxy-indan-1-yl)-5-imidazolecarboxylic acid methyl ester in form of a 1:1-mixture of the 1,3-cis- and 1,3-trans-isomers.

EXAMPLE 33 a) A mixture of 21 parts of 2,3-dihydro-3-methyl-1H-inden-1-one, 25 parts of methyl 2-aminoacetate, 2 parts of a solution of thiophene in methanol 4%, 25 parts of sodium formate and 480 parts of methanol is hydrogenated in a Parr-apparatus and at 50° C. with 5 parts of palladium-on-charcoal catalyst 10%. The reaction mixture is evaporated. The residue is taken up in water and 1,1'-oxybisethane is added. The separated organic layer is extracted with a hydrochloric acid solution 10%. The aqueous layer is made alkaline and the product is extracted with 1,1'-oxybisethane. The combined extracts are dried, filtered and evaporated, yielding 19 parts (54.1%) of methyl N-(2,3-dihydro-3-methyl-1H-inden-1-yl)glycine as a residue.

b) A solution of 17 parts of methyl N-(2,3-dihydro-3-methyl-1H-inden-1-yl)glycine in 60 parts of formic acid and 20 parts of acetic acid anhydride is stirred overnight at room temperature. The reaction mixture is evaporated in vacuo and the residue is taken up in 1,1'-oxybisethane. The organic layer is washed with a sodium hydrogen carbonate solution and water dried, filtered and evaporated. The residue is crystallized from a mixture of 2,2'-oxybispropane and hexane. The product is filtered off and dried, yielding 15 parts (78.7%) of methyl N-(2,3-dihydro-3-methyl-1H-inden-1-yl)-N-formylglycine.

c) To a stirred solution of 15 parts of methyl N-(2,3-dihydro-3-methyl-1H-inden-1-yl)-N-formylglycine in 45 parts of tetrahydrofuran are added 3 parts of a sodium hydride dispersion 50%. After stirring for 10 minutes at room temperature, 15 parts of methyl formate are added and stirring is continued for 5 hours. The precipitated product is filtered off, stirred in water and 1,1'-oxybisethane. The separated aqueous layer is acidified and the product is extracted with trichloromethane. The combined organic layers are evaporated. The residue is dissolved in 120 parts of methanol and 12 parts of concentrated hydrochloric acid are added. Water is added dropwise till the mixture becomes turbid. A solution of 15 parts of potassium thiocyanate in 10 parts of water is added and the whole is stirred overnight at room temperature. The precipitated product is filtered off and dried, yielding 11.5 parts (66.4%) of methyl 1-(2,3-dihydro-3-methyl-1H-inden-1-yl)-2-mercapto-1H-imidazole-5-carboxylate; mp. 176.6° C. (compound 2.34).

d) A mixture of 10 parts of methyl 1-(2,3-dihydro-3-methyl-1H-inden-1-yl)-2-mercapto-1H-imidazole-5-carboxylate and 120 parts of a nitric acid solution 30% is stirred for 30 minutes at room temperature (intense reaction). The reaction mixture is poured into crushed ice and treated with a sodium hydroxide solution. The product is extracted with trichloromethane. The extract is washed with water, dried, filtered and evaporated. The residue is converted into the nitrate salt in 2-propanone and 2,2'-oxybispropane. The salt is filtered off and dried, yielding 6.8 parts (62.6%) of methyl 1-(2,3-dihydro-3-methyl-1H-inden-1-yl)-1H-imidazole-5-carboxylate mononitrate; mp. 140.3° C. (compound 2.35).

e) A solution of 3.6 parts of methyl 1-(2,3-dihydro-3-methyl-1H-inden-1-yl)-1H-imidazole-5-carboxylate mononitrate in 50 parts of a sodium hydroxide solution 20% is stirred for 1.5 hours at reflux temperature. After cooling, the reaction mixture is neutralized with acetic acid. The product is extracted with 1,1'-oxybisethane. The extract is dried, filtered and evaporated. The residue is crystallized from 2,2'-oxybispropane. The product is filtered off and dried, yielding 2.4 parts (90.0%) of 1-(2,3-dihydro-3-methyl-1H-inden-1-yl)-1H-imidazole-5-carboxylic acid; mp. 209.3° C. (compound 2.36).

EXAMPLE 34 a) Following the same procedure of example 33e), methyl 1-(1,2,3,4-tetrahydro-1-naphthalenyl)-1H-imidazole-5-carboxylate is converted into 1-(1,2,3,4-tetrahydro-1-naphthalenyl)-1H-imidazole-5-carboxylic acid; mp. 206.5°-210° c. (compound 1.41).

b) 4.8 Parts of 1-(1,2,3,4-tetrahydro-1-naphthalenyl)-1H-imidazole-5-carboxylic acid are dissolved in 94 parts of warm N,N-dimethylformamide. 0.96 Parts of a sodium hydride dispersion 50% are added portionwise to the thus obtained reaction mixture. Upon complete addition, stirring is continued for 1 hour at room temperature. After the addition of 2.0 parts of 1-chloro-2-methoxyethane, the whole is stirred overnight at 90° C. The reaction mixture is evaporated and the residue is taken up in water. The product is extracted with trichloromethane. The extract is dried, filtered and evaporated, yielding 2.8 parts (46.7%) of (2-methoxyethyl) 1-(1,2,3,4-tetrahydro-1-naphthalenyl)-1H-imidazole-5-carboxylate; mp. 66.8° C. (compound 1.83).

All other compounds listed in the Tables 1 through 21 can be obtained by analogous methods of preparation.

What is claimed is:

1. A compound selected from the group consisting of 1-(2,2-dimethylindan-1-yl)-5-imidazolecarboxylic acid methyl ester, a stereoisomeric form thereof, and an acid addition salt thereof with the proviso that the stereoisomeric form is not the S enantiomer.

2. The compound of claim 1 wherein said compound is R-1-(2,2-dimethylindan-1-yl)-5-imidazolecarboxylic acid methyl ester or an acid addition salt thereof.

3. A method for controlling weeds, which method comprises applying to said weeds or to the locus thereof a herbicidally effective amount of a compound selected from the group consisting of 1-(2,2-dimethylindan-1-yl)-5-imidazolecarboxylic acid methyl ester, a stereoisomeric form thereof, and an acid addition salt thereof with the proviso that the stereoisomeric form is not the S enantiomer.

4. The method of claim 3 wherein said compound is R-1-(2,2-dimethylindan-1-yl)-5-imidazolecarboxylic acid methyl ester or an acid addition salt thereof.

5. A method according to claim 3, wherein the weeds are controlled in crops of useful plants.

6. A method according to claim 5, wherein the crops are selected from sugar beet, rape, soybeans, cotton, sunflower, cereals, especially wheat, barley, rye and oats, rice and maize.

7. A method according to claim 5, wherein the crops are rice, maize or cereals.

8. A method according to claim 7, wherein the crop is rice.

9. A method according to claim 8, wherein the rice plants are transplanted rice plantlets.

10. A method according to claim 8 wherein 0.01 to 5.0 kg of the active ingredient is applied per hectare to areas where rice crops are grown.

11. A method according to claim 10, wherein 0.02 to 1.0 kg of the active ingredient is applied per hectare, after transplanting the rice plantlets.

12. A herbicidal composition, containing inert carriers and, if desired, other adjuvants, and as active ingredient, a herbicidally effective amount of a compound selected from the group consisting of 1-(2,2-dimethylindan-1-yl)-5-imidazolecarboxylic acid methyl ester, a stereoisomeric form thereof, and an acid addition salt thereof with the proviso that the stereoisomeric form is not the S enantiomer.

13. The herbicidal composition of claim 12 wherein said compound is R-1-(2,2-dimethylindan-1-yl)-5-imidazolecarboxylic acid methyl ester or an acid addition salt thereof.

* * * * *